(12) United States Patent  (10) Patent No.: US 8,865,655 B2
Ganesan et al.  (45) Date of Patent: Oct. 21, 2014

(54) DEPSIPEPTIDES AND THEIR THERAPEUTIC USE

(75) Inventors: Arasu Ganesan, Hampshire (GB); Graham Keith Packham, Wiltshire (GB); Alexander Richard Liam Cecil, Hampshire (GB)

(73) Assignee: Karus Therapeutics Limited, Hampshire (GB)

( * ) Notice: Subject to any disclaimer, the term of this patent is extended or adjusted under 35 U.S.C. 154(b) by 1093 days.

(21) Appl. No.: 12/516,110

(22) PCT Filed: Nov. 22, 2007

(86) PCT No.: PCT/GB2007/004472
§ 371 (c)(1),
(2), (4) Date: May 22, 2009

(87) PCT Pub. No.: WO2008/062201
PCT Pub. Date: May 29, 2008

(65) Prior Publication Data
US 2010/0056435 A1 Mar. 4, 2010

(30) Foreign Application Priority Data

Nov. 22, 2006 (GB) .................................. 0623357.1
Nov. 23, 2006 (GB) .................................. 0623331.6

(51) Int. Cl.
C07K 7/54 (2006.01)
A61K 38/12 (2006.01)
A61P 17/02 (2006.01)
C07K 5/103 (2006.01)
C07K 5/02 (2006.01)

(52) U.S. Cl.
CPC .......... *C07K 5/0205* (2013.01); *G01N 2410/10* (2013.01); *G01N 2500/00* (2013.01); *C07K 5/1008* (2013.01); *G01N 2333/98* (2013.01); *C07K 5/101* (2013.01)
USPC .......... 514/21.1; 530/317; 514/9.4; 424/78.06

(58) Field of Classification Search
None
See application file for complete search history.

(56) References Cited

U.S. PATENT DOCUMENTS 6,670,326 B1 * 12/2003 Nagai et al. ................... 514/19.3
7,977,304 B2 * 7/2011 Ganesan et al. ............... 514/1.1

FOREIGN PATENT DOCUMENTS

| EP | 1 142 905 | * 10/2001 |
| EP | 1 142 905 A | 10/2001 |
| EP | 1 302 476 A | 4/2003 |
| EP | 1 547 617 A | 6/2005 |
| EP | 1 548 026 A | 6/2005 |

| WO | WO 01/42282 A | 6/2001 |
| WO | WO 2006/129105 A | 12/2006 |
| WO | WO 2007/040522 A | 4/2007 |
| WO | WO 2007/061939 A | 5/2007 |

OTHER PUBLICATIONS

Yurek-George, 2004, JACS, 126, 1030-1031.*
Miller, 2004, Expert Opin. Ther. Patents, 14, 791-804.*

(Continued)

*Primary Examiner* — Satyanarayana R Gudibande
(74) *Attorney, Agent, or Firm* — Saliwanchik, Lloyd & Eisenschenk

(57) ABSTRACT

A compound of the general Structure (VII) or (VIII) including isoteres and pharmaceutically acceptable salts thereof, wherein $R_1$, $R_2$ (where X=—$CONR_6$—), $R_3$ and $R_7$ are the same or different and each represents an amino-acid side chain moiety; $R_2$ (where X=—CHZ—), $R_4$ and $R_6$ are the same or different and each represents hydrogen, $C_1$-$C_6$ alkyl, $C_2$-$C_6$ alkenyl, or $C_2$-$C_6$ alkynyl; K represents a linear or branched chain of carbon atoms and containing 1-10 atoms; L represents a moiety capable of chelating zinc in the active site of a histone deacetylase (HDAC) or of conversion to such a moiety in vivo (by hydrolysis or reduction, for example); M is a linear or branched chain of carbon or other atoms and containing 1-10 atoms, and capable of undergoing in vivo cleavage to give Structure (VII); and Z is a heteroatom bonded to the macrocycle by a single or double bond, and any other group bonded to Z is H or a protecting group.

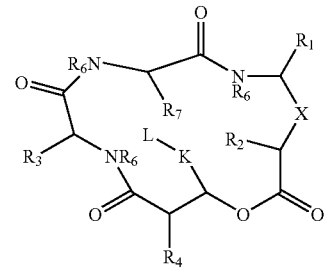

(VII)

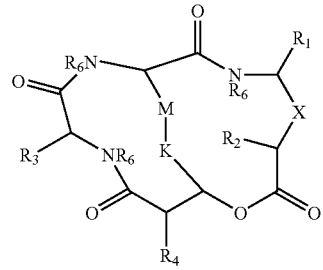

(VIII)

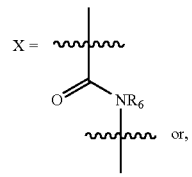 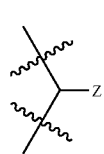

24 Claims, No Drawings

(56) References Cited

OTHER PUBLICATIONS

Furumai, R., et al., "FK228 (depsipeptide) as a natural prodrug that inhibits class I histone deacetylases" *Cancer Research*, Sep. 1, 2002, pp. 4916-4921, vol. 62, No. 17.

Masuoka, Y., et al., "Spiruchostatins A and B, novel gene expression-enhancing substances produced by *Pseudomonas* sp" Tetrahedron Letters, Jan. 1, 2001, pp. 41-44, vol. 42, No. 1.

Xiao, J.J., et al., "Identification of Thiols and Glutathione Conjugates of Depsipeptide FK228 (FR901228), a Novel Histone Protein Deacetylase Inhibitor, in the Blood" *Rapid Communications in Mass Spectrometry*, 2003, pp. 757-766, vol. 17.

Yurek-George, A., et al., "Total synthesis of sp ruchostatin A, a potent histone deacetylase inhibitor" *J. of the American Chemical Society*, Feb. 4, 2004, pp. 1030-1031, vol. 126, No. 4.

Yurek-George, A., et al., "The first biologically active synthetic analogues of FK228, the depsipeptide histone deacetylase inhibitor" *J. of Medicinal Chemistry*, Nov. 15, 2007, pp. 5720-5726, vol. 50, No. 23.

\* cited by examiner

DEPSIPEPTIDES AND THEIR THERAPEUTIC USE

This application is a National Stage Application of International Application Number PCT/GB2007/004472, filed Nov. 22, 2007; which claims priority to Great Britain Application No. 0623357.1, filed Nov. 22, 2006 and Great Britain Application No. 0623331.6, filed Nov. 23, 2006; which are incorporated herein by reference in their entirety.

FIELD OF THE INVENTION

The present invention relates to depsipeptides which act as inhibitors of histone deacetylase (HDAC) and therefore have therapeutic utility.

BACKGROUND OF THE INVENTION

HDACs are zinc metalloenzymes that catalyse the hydrolysis of acetylated lysine residues. In histones, this returns lysines to their protonated state and is a global mechanism of eukaryotic transcriptional control, resulting in tight packaging of DNA in the nucleosome. Additionally, reversible lysine acetylation is an important regulatory process for non-histone proteins. Thus, compounds which are able to modulate HDAC have important therapeutic potential.

The natural products FK228 (Structure I) and Spiruchostatin A (Structure II) are depsipeptides that have been reported to have potential as HDAC inhibitors. The term depsipeptide describes a class of oligopeptides or polypeptides that have both ester and peptide links the chain.

FK228 is a cyclic depsipeptide containing 4 monomer units together with a cross-ring bridge. This compound, under the trade name of Romidepsin®, has been tested as a therapeutic in human trials and shown that it has valuable effects on a number of diseases.

Spiruchostatin A is a cyclic depsipeptide that is structurally related to FK228: it is a cyclic depsipeptide containing a tri-peptide, a statine unit and a cross-ring bridge.

Structure I

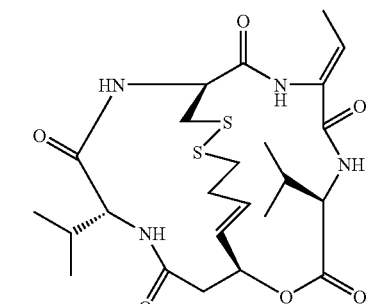

Structure II

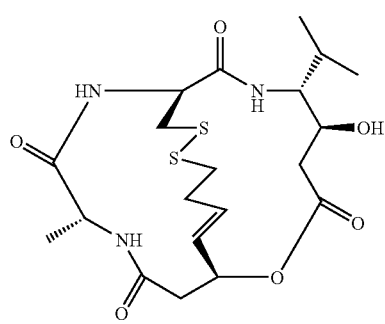

However, because both FK228 and Spiruchostatin A are natural products, they are not amenable to optimization for use as a therapeutic agent.

Analogues of these compounds are disclosed in WO2006/129105 (published after the priority dates claimed); further such compounds are disclosed in an unpublished PCT Application claiming priority from GB Patent Application No. 0623388.6. They may have improved HDAC inhibitory properties with respect to FK228 and Spiruchostatin A or other drug-like properties which make them more useful as medicines. These compounds have the general structures shown in Structures III, IV, V & VI wherein $R_1$, $R_2$, $R_3$ and $R_4$ are the same or different and represent an amino acid side chain moiety, each $R_6$ is the same or different and represents hydrogen or $C_1$-$C_6$ alkyl, $C_2$-$C_6$ alkenyl or $C_2$-$C_6$ alkynyl, and $Pr^1$ and $Pr^2$ are the same or different and represent hydrogen or a thiol-protecting group.

Without being constrained by theory, it is believed that Structure IV where $R_1$ is =CH—$CH_3$, $R_2$ is —CH($CH_3$)$_2$, $R_3$ is —CH($CH_3$)$_2$, $R_4$ and $R_6$ are both —H and $Pr^1$ and $Pr^2$ are both —H, is formed inside the cell from Structure I by reduction of the disulphide bond, and that the 4-thio-butyl-1-ene so formed is a critical part of the mechanism of action of the compound. Thus it has previously been suggested that compounds lacking this group will have reduced utility as therapeutic agents.

Structure III

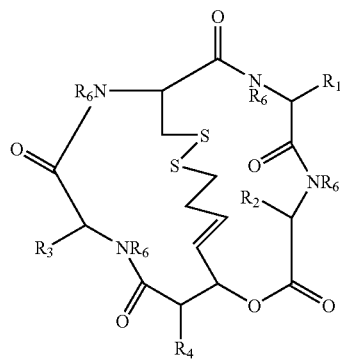

Structure IV

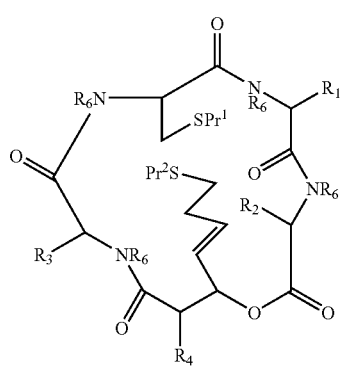

Structure V

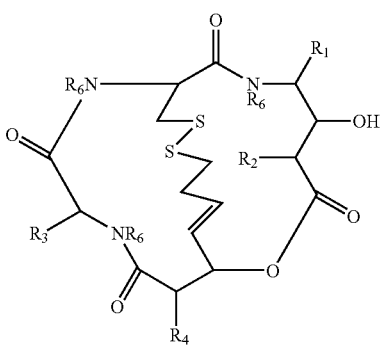

Structure VI

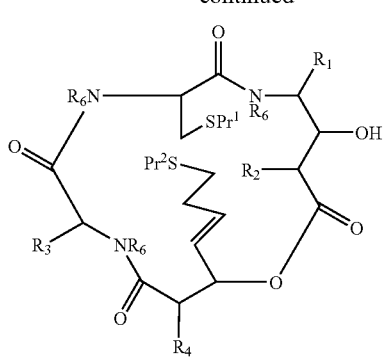

This concept is supported by the observation that FR-901375, a cyclic depsipeptide HDAC inhibitor with quite a different ring structure, has the same disulphide-containing bridge across the ring as is seen in FK228 and Spiruchostatin A.

SUMMARY OF THE INVENTION

The present invention provides analogues of Structures I to VI, and of structures related to them in ways that will be apparent to those skilled in the art in which the 'bridge' structure is different from that of other depsipeptides and which, surprisingly, are found to be effective inhibitors of HDAC enzymes, and have properties which indicate that they may have greater potential as treatments for human disease. These compounds are hereinafter designated members of the class of compounds called Bridge Variant Depsipeptides (BVDs).

This class of BVDs is defined by Structures VII & VIII:

Structure VII

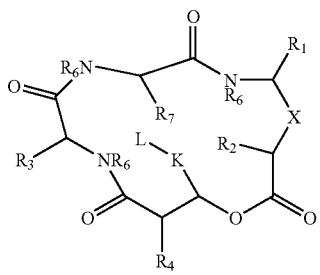

Structure VIII

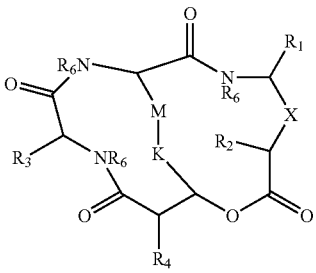

$R_1$, $R_2$, $R_3$, $R_4$ and $R_6$ have the meanings ascribed above;

K represents a linear or branched chain of carbon atoms linked by bonds some of which may be single bonds and some of which may be double bonds and some of which may be a triple bond and containing 1-10 atoms, such that Structure VII does not form Structure IV (where $R_1$ is =CH—$CH_3$, $R_2$ is —$CH(CH_3)_2$, $R_3$ is —$CH(CH_3)_2$, and $R_4$, $R_6$, $Pr^1$, $Pr^2$ are all —H) or Structure VI (where $R_1$ is —$CH(CH_3)_2$, $R_2$ is —H, $R_3$ is —$CH_3$, and $R_4$, $R_6$, $Pr^1$, $Pr^2$ are all —H), and Structure VIII does not form Structure I or II;

L represents a moiety capable of chelating zinc in the active site of an HDAC or a moiety that is capable of becoming a moiety capable of chelating zinc in the active site of an HDAC in vivo (by hydrolysis or reduction, for example) and includes S and $SPr^1$, where $Pr^1$ has the meaning ascribed above such that Structure VIII does not form Structure I (FK228) or Structure II (Spiruchostatin A) or Structure VII does not form Structure IV (the reduced form of FK228, where $R_1$ is =CH—$CH_3$, $R_2$ is $CH(CH_3)_2$, $R_3$ is $CH(CH_3)_2$, $R_4$ and $R_6$ are H, X is —C(O)$NR_6$—, K is —CH=$CHCH_2CH_2$—, L is —SH and $R_7$ is —$CH_2SH$ or Structure VII does not form Structure VI (the reduced form of Spiruchostatin A, where $R_1$ is —$CH(CH_3)_2$, $R_2$ is H, $R_3$ is $CH_3$, $R_4$ and $R_6$ are H, X is —CHZ—, Z is —OH, K is —CH=$CHCH_2CH_2$—, L is SH and $R_7$ is —$CH_2SH$);

$R_7$ represents an amino-acid group side chain, the group —X or the group —W—X, where W is a linear or branched chain of carbon atoms linked by bonds some of which may be single bonds and some of which may be double bonds and some of which may be a triple bond and containing 1-10 atoms, and X is one of —H, —$NH_2$, N—$R_6$, N—$(R_6)_2$—OH, —O—$R_6$, -Halogen, S—$Pr^2$, where $R_6$, S and $Pr^2$ have the same meaning as defined above, such that Structure VII does not form Structure IV (the reduced form of FK228, where $R_1$ is =CH—$CH_3$, $R_2$ is $CH(CH_3)_2$, $R_3$ is $CH(CH_3)_2$, $R_4$ and $R_6$ are H, X is —C(O)$NR_6$—, K is —CH=$CHCH_2CH_2$—, L is —SH and $R_7$ is —$CH_2SH$ or Structure VII does not form Structure VI (the reduced form of Spiruchostatin A, where $R_1$ is —$CH(CH_3)_2$, $R_2$ is H, $R_3$ is $CH_3$, $R_4$ and $R_6$ are H, X is —CHZ—, Z is —OH, K is —CH=$CHCH_2CH_2$—, L is SH and $R_7$ is —$CH_2SH$) and, M is a linear or branched chain of carbon or other atoms linked by bonds some of which may be single bonds and some of which may be double bonds and some of which may be a triple bond and containing 1-10 atoms, such that the in vivo cleavage of any bond within M results in Structure VII, such that Structure VIII does not form Structures I or II and Structure VII formed by the in vivo cleavage of Structure VIII does not form Structure I (FK228) or Structure II (Spiruchostatin A).

Z is a species containing -Q-$Pr^3$ or -Q($Pr^3$)$Pr^4$ where Q is a heteroatom such that the heteroatom is adjoined directly to the macrocycle of the depsipeptide, for example =O, —$OPr^3$, —N($Pr^3$)$Pr^4$, —$SPr^3$ and where $Pr^3$ and $Pr^4$ are the same or different and represent either a thiol protecting group, a hydrogen or a heteroatom-protecting group, examples of which may include an ether, an ester, an amide, a thioether or a thioester.

The present invention further provides the use of a BVD as defined above or a pharmaceutically acceptable salt thereof, in the manufacture of a medicament for use as an inhibitor of HDAC.

DESCRIPTION OF THE INVENTION

Synthesis of compounds of Structures VII and VIII is typically conducted using amino acids of which —CO—CR—NH— forms part of the macrocycle and R is a side-chain moiety. $R_1$, $R_2$, (in Structures VII and VIII where X=—$CONR_6$—) $R_3$ and $R_7$ may be introduced in this way. $R_2$ (in Structures VII and VIII where X=—CHZ—) and $R_4$ may be also be such moieties even though they may not be derived from an amino acid as such.

As used herein, the term "amino acid side chain moiety" refers to any side chain that may be present in natural and unnatural amino acids Examples of amino acid side chain moieties derived from unnatural amino acids, with the amino acids from which they are derived shown in brackets, are —$(CH_2)_2$—C(O)—O—$C(CH_3)_3$ (tert-butoxy-carbonylmethylanaline), —$(CH_2)_4$—NH—C(O)—O—$C(CH_3)_3$ ($N_\epsilon$-(tert-butoxycarbonyl)-lysine), —$(CH_2)_3$—NH—$C(O)NH_2$ (citrulline), —$CH_2$—$CH_2OH$ (homoserine) and —$(CH_2)_2$—$CH_2NH_2$ (ornithine).

A $C_1$-$C_6$ alkyl group or moiety can be linear or branched. Typically, it is a $C_1$-$C_4$ alkyl group or moiety, for example methyl, ethyl, n-propyl, i-propyl, n-butyl, sec-butyl and t-butyl. Preferred examples include methyl, i-propyl and t-butyl.

A $C_2$-$C_6$ alkenyl group or moiety can be linear or branched. Typically, it is a $C_2$-$C_4$ alkenyl group or moiety. It is preferred that the alkenyl radicals are mono or diunsaturated, more preferably monounsaturated. Examples include vinyl, allyl, 1-propenyl, isopropenyl, 1-butenyl, 2-butenyl and 3-butenyl.

A $C_2$-$C_6$ alkynyl group or moiety can be linear or branched. Typically, it is a $C_2$-$C_4$ alkynyl group or moiety.

A thiol-protecting group is typically:

(a) a protecting group that forms a thioether to protect a thiol group, for example a benzyl group which is optionally substituted by $C_1$-$C_6$ alkoxy (for example methoxy), $C_1$-$C_6$ acyloxy (for example acetoxy), hydroxy and nitro, picolyl, picolyl-N-oxide, anthrylmethyl, diphenylmethyl, phenyl, t-butyl, adamanthyl, $C_1$-$C_6$ acyloxymethyl (for example pivaloyloxymethyl, tertiary butoxycarbonyloxymethyl);

(b) a protecting group that forms a monothio, dithio or aminothioacetal to protect a thiol group, for example $C_1$-$C_6$ alkoxymethyl (for example methoxymethyl, isobutoxymethyl), tetrahydropyranyl, benzylthiomethyl, phenylthiomethyl, thiazolidine, acetamidemethyl, benzamidomethyl;

(c) a protecting group that forms a thioester to protect a thiol group, such as tertiary butoxycarbonyl (BOC), acetyl and its derivatives, benzoyl and its derivatives; or, (d) a protecting group that forms a carbamine acid thioester to protect a thiol group, such as carbamoyl, phenylcarbamoyl, $C_1$-$C_6$ alkylcarbamoyl (for example methylcarbamoyl and ethylcarbamoyl).

Typically, $Pr^1$ and $Pr^2$ are the same or different and each represent hydrogen or a protecting group that forms a thioether, a monothio, dithio or aminothioacetal, a thioester or a carbamine acid thioester to protect a thiol group.

Typically, $Pr^3$ and $Pr^4$ are the same or different and each represent hydrogen or a each represent hydrogen or a protecting group that forms a thioether, a monothio, dithio or aminothioacetal, a thioester or a carbamine acid thioester to protect a thiol group or a protecting group that forms an ether, an ester, an acetal, a phosphate or a sulphate to protect a hydroxyl group, or a protecting group that forms an amino or an amide to protect an amine group.

The particular nature of the group L is not critical, provided that it has the given functional, and a wide variety of suitable groups will be apparent to one of ordinary skill in the art. They include not only S or $SPr^1$ (where $Pr^1$ is H or a thiol-protecting group), but also groups such as —C(O)OH, —C(O)$OPr^5$ (where $Pr^5$ is a protecting group capable of forming an ester), —C(O)NHOH, —C(O)$NHOPr^6$ (where $Pr^6$ is a hydroxamic-acid protecting group), —C(O)$NH_2$, —C(O)$NHR_8$ (where $R_8$ is an alkyl, alkenyl, aryl or heteroaryl group), or —C(O)$N(R_8)R_9$ (where $R_8$ and $R_9$ are the same or different and are alkyl, alkenyl, aryl or heteroaryl groups);

In one embodiment, the amino acid side chain moieties are those derived from natural amino acids. Examples of amino acid side chain moieties derived from natural amino acids, with the amino acids from which they are derived shown in brackets, are —H (Glycine), —$CH_3$ (Alanine), —$CH(CH_3)_2$ (Valine), —$CH_2CH(CH_3)_2$ (Leucine), —$CH(CH_3)CH_2CH_3$ (Isoleucine), —$(CH_2)_4NH_2$ (Lysine), —$(CH_2)_3NHC(=NH)NH_2$ (Arginine), —$CH_2$-(5-1H-imidazolyl) (Histidine), —$CH_2CONH_2$ (Asparagine), —$CH_2CH_2CONH_2$ (Glutamine), —$CH_2COOH$ (Aspartic acid), —$CH_2CH_2COOH$ (Glutamic acid), —$CH_2$-phenyl (Phenylalanine), —$CH_2$(4-OH-phenyl) (Tyrosine), —$CH_2$-(3-1H-indolyl) (Tryptophan), —$CH_2SH$ (Cysteine), —$CH_2CH_2SCH_3$ (Methioine), —$CH_2OH$ (Serine), and —$CH(OH)CH_3$ (Threonine).

In one embodiment, each amino acid side chain is an amino acid side chain moiety present in a natural amino acid or is —$(CH_2)_2$—C(O)—O—$C(CH_3)_3$ (tert-butoxy-carbonylmethylanaline), —$(CH_2)_4$—NH—C(O)—O—$C(CH_3)_3$ ($N_\epsilon$-(tertbutoxycarbonyl)-lysine), —$(CH_2)_3$—NH—$C(O)NH_2$ (citrulline), —$CH_2$—$CH_2OH$ (homoserine) or —$(CH_2)_2$—$CH_2NH_2$ (ornithine).

In one preferred embodiment of the invention, $R_1$ is —$CH(CH_3)_2$, $R_2$ is —H, $R_3$ is —$CH(CH_3)_2$, $R_4$ is —H, $R_6$ is —H, $R_7$ is —$CH_3$, X is —CH(Z)—, Z is —OH, K is —CH=$CHCH_2CH_2$— and L is —S—C(O)$CH_3$ and shown in the Examples as Compound 10.

In another preferred embodiment of the invention, $R_1$ is —$CH(CH_3)_2$, $R_2$ is —H, $R_3$ is —$CH(CH_3)_2$, $R_4$ is —H, $R_6$ is —H, $R_7$ is —$CH_3$, X is —CH(Z)—, Z is —OH, K is —CH=$CHCH_2CH_2$— and L is —SH and shown in the Examples as Compound 9.

In another preferred embodiment of the invention, $R_1$ is —$CH(CH_3)_2$, $R_2$ is —H, $R_3$ is —$CH_3$, $R_4$ is —H, $R_6$ is —H, $R_7$ is —$CH_2Ph$, X is —$CONR_6$—, K is —CH=$CHCH_2CH_2$— and L is —S—C(O)$CH_3$ and shown in the Examples as Compound 17.

In one embodiment each amino acid side chain is selected from —H, —$C_1$-$C_6$ alkyl, —$C_2$-$C_6$ alkenyl, -L'-O—C(O)—R', -L'-C(O)—O—R", -L'-NR"R", -L'-Het-C(O)-Het-R" and -L'-Het-R", wherein L' is a $C_1$-$C_6$ alkylene group, A is phenyl or a 5- to 6-membered heteroaryl group, each R' is the same or different and represents $C_1$-$C_4$ alkyl, each R" is the same or different and represents H or $C_1$-$C_6$ alkyl, each Het is the same or different and is a heteroatom spacer selected from —O—, —N(R''')— and —S—, and each R''' is the same or different and represents H or $C_1$-$C_4$ alkyl.

In another preferred embodiment of the invention, $R_1$ is —$CH(CH_3)_2$, $R_2$ is —H, $R_3$ is —$CH_3$, $R_4$ is —H, $R_6$ is —H, $R_7$ is —$CH_2Ph$, X is —$CONR_6$—, K is —CH=$CHCH_2CH_2$— and L is —SH and shown in the Examples as Compound 16.

As used herein, a pharmaceutically acceptable salt is a salt with a pharmaceutically acceptable acid or base. Pharmaceutically acceptable acids include both inorganic acids such as hydrochloric, sulphuric, phosphoric, diphosphoric, hydrobromic or nitric acid and organic acids such as citric, fumaric, maleic, malic, ascorbic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases such as alkyl amines, aralkyl amines or heterocyclic amines.

As used herein, the term "isostere" refers to a compound resulting from the exchange of an atom or a group of atoms with another, broadly similar, atom or group of atoms. In the compounds of Structures VII or VIII, the moieties which contain isosteric groups are preferably —NR$_6$—CHR$_1$—CO— (or —NR$_6$—CHR$_1$—CH(OR$_8$)—), —NR$_6$—CHR$_2$—CO—O— (or —CHR$_2$—CO—O—) and —NR$_6$—CO—CHR$_3$—NR$_6$—CO—. In the compounds of Structure VII or VIII, the moieties which contain isosteric groups are more preferably —NR$_6$—CHR$_1$—CO— (or —NR$_6$—CHR$_2$—CH(OR$_8$)—) and —NR$_6$—CHR$_2$—CO—O— (or —CHR$_2$—CO—O—). Examples of such isosteres are compounds of Structures VII or VIII wherein the moiety —NH— has been replaced by —CH$_2$—, —O— or —S—, the moiety —CO— has been replaced by —S— or (=N$^+$H)— and the moiety —O— has been replaced by —S—, CH$_2$— or —NH—.

For the avoidance of doubt, the present invention also embraces pro-drugs which react in vivo to give a compound of the present invention or an isostere or pharmaceutically acceptable salt thereof.

The BVD may be prepared by conventional routes, for example using the following schemes wherein the groups R$_1$ to R$_7$, L, K, M and Z are as defined above:

R$_2$ and then reduced to give a statine unit. In step (b), the statine is condensed with an amino-acid bearing the side-chain R$_7$ to give a tripeptide isostere. In step (c) the tripeptide isostere is coupled with an amino-acid bearing the side-chain R$_3$ to provide a tetrapeptide isostere. In step (d), the N-terminus of the peptide is deprotected, and the free amine is coupled with a □-hydroxy acid derivative wherein R$_5$ is a temporary blocking group which can be removed to produce a compound wherein R$_5$ is H, and LG is either a leaving group in the form of (for example) a chiral auxiliary as reported in Yurek-George, A.; Habens, F.; Brimmell, M.; Packham, G.; Ganesan, A. *J. Am. Chem. Soc.* 2004, 126, 1030-1031 or LG is an alcohol thus giving the free acid which allows for standard amide coupling. In step (e), the ester group is hydrolysed, followed by cyclization in step (f). Further chemical transformation of the Zinc binding group, L, may be carried out to protect the Zinc binding group, for example the transformation of —SH to SPr$^2$.

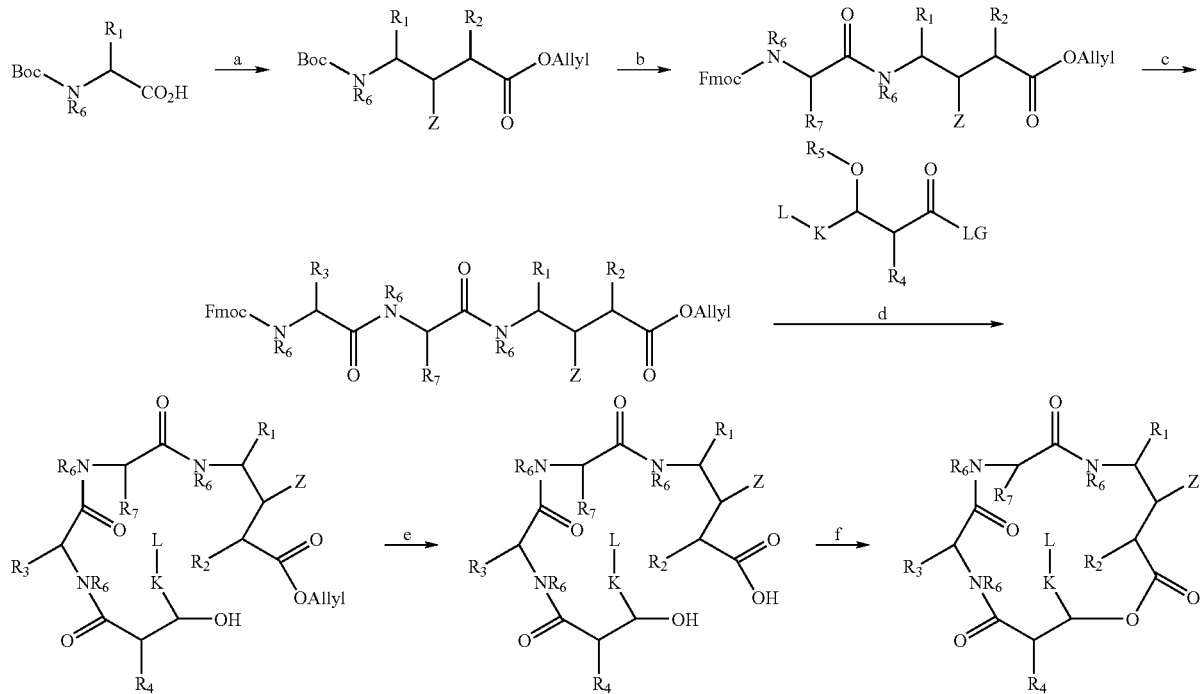

Scheme 1

In Scheme 1, step (a), an amino-acid bearing the side-chain R$_1$ is condensed with an ester enolate bearing the side-chain

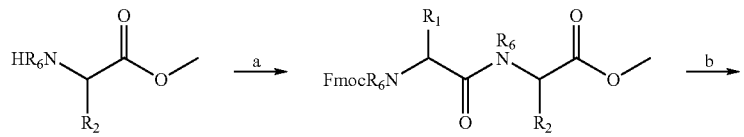

Scheme 2

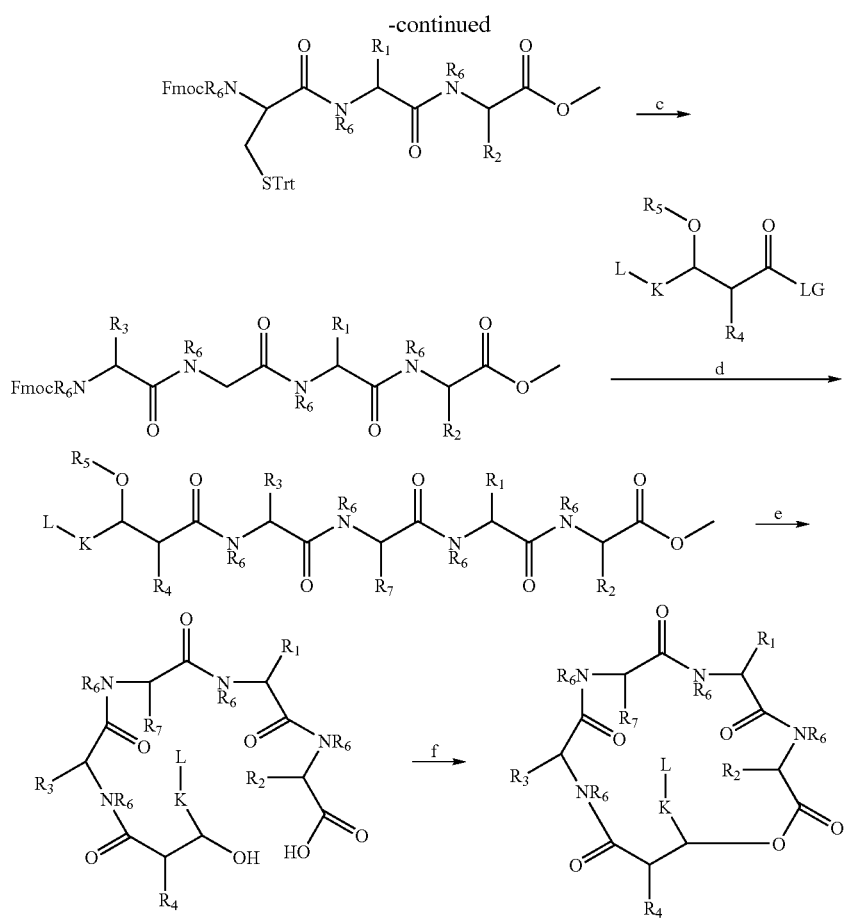

In Scheme 2, step (a), an amino acid ester bearing the side-chain $R_2$ is condensed with a second amino acid bearing the side-chain $R_1$ to give a dipeptide. In step (b), the dipeptide is coupled with a third amino acid bearing the side chain $R_7$ to give a tripeptide. In step (c) the tripeptide is coupled with an amino acid to provide a protected tetrapeptide. In step (d), the N-terminus of the peptide is deprotected, and the free amine is coupled with a β-hydroxy acid derivative wherein $R_5$ is a temporary blocking group which can be removed to produce a compound wherein $R_5$ is H, and LG is either a leaving group in the form of (for example) a chiral auxiliary as reported in Yurek-George, A.; Habens, F.; Brimmell, M.; Packham, G.; Ganesan, A. *J. Am. Chem. Soc.* 2004, 126, 1030-1031 or LG is an alcohol thus giving the free acid which allows for standard amide coupling. In step (e), the ester group is hydrolysed, followed by cyclization in step (f). Further chemical transformation of the Zinc binding group, L, may be carried out to protect the Zinc binding group, for example the transformation of —SH to $SPr^2$.

Compounds of the invention in which $R_6$ is other than hydrogen can be obtained either by alkylating a corresponding compound of the invention or intermediate in which $R_6$ is hydrogen or by using appropriately substituted starting materials.

Compounds of formula VIII can be prepared when $R_7$ and L are connected to make the group M.

As the skilled person will appreciate, when one of $R_1$, $R_2$, $R_3$, $R_4$, $R_6$, $R_7$, L, K and Z carries a functional group such as —OH, —SH, —$NH_2$ or —COOH, then it may be preferred for that group to be protected for one or more of the reaction steps following its introduction. In this case the group in question could be protected in a separate step after its introduction, or, it could be protected already at the time it is introduced. The skilled person will be aware of suitable protecting groups that can be used in this regard.

The thus obtained BVD analogues may be salified by treatment with an appropriate acid or base. Racemic mixtures obtained by any of the above processes can be resolved by standard techniques, for example elution on a chiral chromatography column.

Preferred compounds of the invention have an HDAC inhibitory activity which is at least equal to that exhibited by Suberoylanilide hydroxamic acid (SAHA). Thus, in a further embodiment, the present invention provides a process for selecting a compound which has an HDAC inhibitory activity which is at least equal to that exhibited by SAHA, which process comprises preparing a compound of Formula VII or VIII by:

(i) either reacting a compound of formula (X) with a compound of formula (XI)

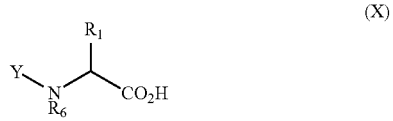

-continued

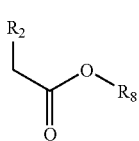
(XI)

wherein $R_1$, $R_2$ and $R_6$ are as defined above, $R_8$ is $C_1$-$C_4$ alkyl or $C_2$-$C_4$ alkenyl and Y is an amino protecting group;

or, (i) reacting a compound of formula (XII) with a compound of (XIII)

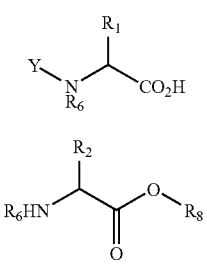
(XII)

(XIII)

wherein $R_1$, $R_2$ and $R_6$ are as defined above, $R_8$ is $C_1$-$C_4$ alkyl or $C_2$-$C_4$ alkenyl and Y is an amino protecting group;

(ii) deprotecting the thus obtained intermediate and reacting it with a compound of formula (XIV)

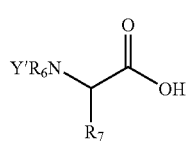
(XIV)

wherein $R_6$ and $R_7$ are defined above, Y' is an amino protecting group;

(iii) deprotecting the thus obtained intermediate and reacting it with a compound of formula (XV)

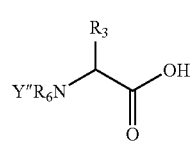
(XV)

wherein $R_3$ and $R_6$ are defined above and Y" is an amino protecting group;

(iv) deprotecting the thus obtained intermediate and reacting it with a compound of formula (XVI)

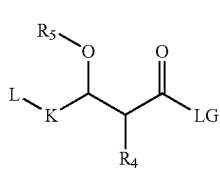
(XVI)

wherein $R_4$, $R_5$, K and L are defined above, $R_5$ is hydrogen or a hydroxy protecting group, LG is a leaving group;

(v) optionally deprotecting the β-hydroxy group on the thus obtained intermediate to remove the $R_5$ protecting group and replace it with H;

(vi) hydrolysing and cyclizing the thus obtained intermediate;

(vii) optionally modifying the Zinc binding group, for example by adding a protecting group, $Pr^1$ or $Pr^2$;

(viii) optionally removing any protecting groups present on R1, R2, R3 and R7 and replace them with H; and, (ix) screening the thus obtained compound to measure its activity as an HDAC inhibitor.

Typically, in step (vi), hydrolysis of the ester group is effected before cyclisation.

The person of skill in the art will appreciate that various identities may be used for the protecting groups Y, Y', and Y" and that the preferred identity will depend in each case on the nature of the particular groups present.

The groups Y, Y' and Y" may, for example, be t-butoxycarbonyl (Boc) or 9-fluorenylmethoxycarbonyl (Fmoc). Typically, they are Fmoc.

The skilled person will be aware of suitable identities for the leaving group LG. It may, for example, be a chiral auxiliary, such as a thiazolidinethione group attached via its N atom, as explained in Yurek-George, A. et al (*J. Am. Chem. Soc.* 2004, 126, 1030-1031). Alternatively, it may be a —OH group.

The group $R_8$ is typically a $C_1$-$C_4$ alkyl or $C_1$-$C_4$ alkenyl group. More typically, it is methyl or allyl.

The skilled person will appreciate that various assays are suitable for testing for HDAC inhibition and may be used to measure the activity of a compound obtained from step (viii) compared to that of the known HDAC inhibitor SAHA. Thus, the $IC_{50}$ of a test compound against HDAC can, for example, be determined in an in vitro assay, and compared with the $IC_{50}$ of SAHA under the same assay conditions. If a test compound has an $IC_{50}$ value equal to or lower than that of SAHA it should be understood as having an HDAC inhibitory activity which is at least equal to that exhibited by SAHA.

In a preferred embodiment, the present invention provides a process for selecting a compound which has an HDAC inhibitory activity which is at least equal to that exhibited by SAHA as defined above, wherein in step (ix) the screening step is an in vitro HDAC assay. Typically, said assay comprises contacting a test compound and SAHA, at various concentrations, with diluted Hela Nuclear Extract to determine the $IC_{50}$ of the test compound and of SAHA against Hela Nuclear Extract. A test compound which has an $IC_{50}$ value measured against Hela Nuclear Extract which is equal to, or lower than, the $IC_{50}$ of SAHA under the same assay conditions should be understood as having an inhibitory activity which is at least equal to that exhibited by SAHA. Typically said assay is performed using a HDAC fluorescent activity assay kit (Biomol, UK) and the test compounds are reduced prior to analysis.

In another embodiment, the present invention provides a process for selecting a compound which has a human cancer cell growth inhibitory activity which is at least equal to that exhibited by SAHA, which process comprises preparing a compound of Structure VII or VIII via steps (i) to (viii) as defined above followed by (ix) screening the thus obtained compound to measure its activity as a human cancer cell growth inhibitor.

The skilled person will appreciate that various assays are suitable for testing for human cancer cell growth inhibition and may be used to measure the activity of a compound obtained from step (viii) compared to that of SAHA. Thus, the $IC_{50}$ of a test compound against human cancer cell growth can, for example, be determined in an in vitro assay, and compared with the $IC_{50}$ of SAHA under the same assay conditions. If a test compound has an $IC_{50}$ value equal to or lower than that of SAHA it should be understood as having an inhibitory activity which is at least equal to that exhibited by SAHA. Typically in this embodiment step (ix) comprises an in vitro assay which comprises contacting a test compound and SAHA, at various concentrations, with an MCF7 breast, HUT78 T-cell leukaemia, A2780 ovarian, PC3 or LNCAP prostate cancer cell line to determine the $IC_{50}$ of the test compound and of SAHA against the cell line. A test compound which has an $IC_{50}$ value measured against any of these cell lines which is equal to, or lower than, the $IC_{50}$ of SAHA under the same assay conditions should be understood as having an inhibitory activity at least equal to that of SAHA. Typically in this embodiment, said assay is performed using the CyQuant™ assay system (Moelcular Probes, Inc. USA).

In another preferred embodiment, the present invention provides a process for selecting a compound which has an anti-inflammatory activity which is at least equal to that exhibited by SAHA, which process comprises preparing a compound of Structure VII or VIII via steps (i) to (viii) as defined above followed by (ix) screening the thus obtained compound to measure its anti-inflammatory activity.

The skilled person will appreciate that various assays are suitable for assessing the anti-inflammatory activity of a compound. The anti-inflammatory activity of a test compound relative to SAHA may, for example, be determined by measuring the activity of a compound in inhibiting the production of TNFα from peripheral blood mononuclear cells (PBMCs) relative to SAHA. Thus, the ability of a test compound to inhibit the production of TNFα from PBMCs can, for example, be determined in an assay, and compared with the activity of SAHA under the same assay conditions. If a test compound has an in vitro inhibitory activity of TNFα production which is equal to or higher than that of SAHA under the same assay conditions it should be understood as having an anti-inflammatory activity which is at least equal to that exhibited by SAHA. Typically step (viii) is performed using the Quantikine® Human-α assay kit (R&D systems, Abingdon UK).

In another aspect of this embodiment, the anti-inflammatory activity of a test compound relative to SAHA may be determined by assessing the activity of a compound in inhibiting inflammation in Balb/c mice relative to SAHA. If a test compound has an in vivo inhibitory activity which is equal to or higher than that of SAHA under the same test conditions it should be understood as having an anti-inflammatory activity which is at least equal to that exhibited by SAHA. Typically, in this embodiment step (viii) is performed by assessing the in vivo activity of a test compound and of SAHA in inhibiting inflammation in Balb/c mice induced by a chemical challenge. Typically, said chemical challenge involves the topical administration to the mice of oxalazone or acetone. In this embodiment, the compounds under investigation may be applied before or after the chemical challenge.

In another preferred embodiment, the present invention provides a process for selecting a compound which has an activity in inducing a predominant G2/M phase arrest or cell death in MCF7 cells which is at least equal to that exhibited by SAHA, which process comprises preparing a compound of Structure VII or VIII via steps (i) to (viii) as defined above followed by (ix) screening the thus obtained compound to measure activity in inducing a predominant G2/M phase arrest or cell death in MCF7 cells relative to SAHA.

The compounds of the present invention are found to be inhibitors of HDAC. The compounds of the present invention are therefore therapeutically useful.

A pharmaceutical composition according to the invention comprises a compound of Structure VII or VIII, and a pharmaceutically acceptable diluent or carrier. Such a pharmaceutical composition typically contains up to 85 wt % of a compound of the invention. More typically, it contains up to 50 wt % of a compound of the invention. Preferred pharmaceutical compositions are sterile and pyrogen free. Further, the pharmaceutical compositions provided by the invention typically contain a compound of the invention which is a substantially pure optical isomer. Preferably, the pharmaceutical composition comprises a pharmaceutically acceptable salt of a compound of Structure VII or VIII or an isostere thereof.

The compounds of the invention and compositions comprising them may be administered in a variety of dosage forms. In one embodiment, a pharmaceutical composition comprising a compound of the invention may be formulated in a format suitable for oral, rectal, parenteral, intranasal or transdermal administration or administration by inhalation or by suppository. Typical routes of administration are parenteral, intranasal or transdermal administration or administration by inhalation.

The compounds of the invention can be administered orally, for example as tablets, troches, lozenges, aqueous or oily suspensions, dispersible powders or granules. Preferred pharmaceutical compositions of the invention are compositions suitable for oral administration, for example tablets and capsules.

The compounds of the invention may also be administered parenterally, whether subcutaneously, intravenously, intramuscularly, intrasternally, transdermally or by infusion techniques. The compounds may also be administered as suppositories.

The compounds of the invention may also be administered by inhalation. An advantage of inhaled medications are their direct delivery to the area of rich blood supply in comparison to many medications taken by oral route. Thus, the absorption is very rapid as the alveoli have an enormous surface area and rich blood supply and first pass metabolism is bypassed. A further advantage may be to treat diseases of the pulmonary system, such that delivering drugs by inhalation delivers them to the proximity of the cells which are required to be treated.

The present invention also provides an inhalation device containing such a pharmaceutical composition. Typically said device is a metered dose inhaler (MDI), which contains a pharmaceutically acceptable chemical propellant to push the medication out of the inhaler.

The compounds of the invention may also be administered by intranasal administration. The nasal cavity's highly permeable tissue is very receptive to medication and absorbs it quickly and efficiently, more so than drugs in tablet form. Nasal drug delivery is less painful and invasive than injections, generating less anxiety among patients. By this method absorption is very rapid and first-pass metabolism is usually bypassed, thus reducing inter-patient variability. Further, the present invention also provides an intranasal device containing such a pharmaceutical composition.

The compounds of the invention may also be administered by transdermal administration. The present invention therefore also provides a transdermal patch containing a compound of the invention.

The compounds of the invention may also be administered by sublingual administration. The present invention therefore also provides a sub-lingual tablet comprising a compound of the invention.

A compound of the invention may also be formulated with an agent which reduces degradation of the substance by processes other than the normal metabolism of the patient, such as anti-bacterial agents, or inhibitors of protease enzymes which might be the present in the patient or in commensural or parasite organisms living on or within the patient, and which are capable of degrading the compound.

Liquid dispersions for oral administration may be syrups, emulsions and suspensions.

Suspensions and emulsions may contain as carrier, for example a natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g. sterile water, olive oil, ethyl oleate, glycols, e.g. propylene glycol, and, if desired, a suitable amount of lidocaine hydrochloride.

Solutions for injection or infusion may contain as carrier, for example, sterile water or preferably they may be in the form of sterile, aqueous, isotonic saline solutions.

The compounds of the present invention are therapeutically useful in the treatment or prevention of conditions mediated by HDAC. Accordingly, the present invention provides the use of a compound of the Structure VII or VIII, or a pharmaceutically acceptable salt thereof, in the manufacture of a medicament for use in the treatment or prevention of a condition materially affected by the activity of an HDAC. Also provided is a method of treating a patient suffering from or susceptible to a condition mediated by HDAC, which method comprises administering to said patient an effective amount of a compound of Structure VII or VIII, an isostere thereof or a pharmaceutically acceptable salt thereof.

In one embodiment the compounds of the present invention may be used in combination with another known inhibitor of HDAC, such as SAHA. In this embodiment, the combination product may be formulated such that it comprises each of the medicaments for simultaneous, separate or sequential use.

The present invention therefore also provides the use of a compounds according to Structure VII or VIII or an isostere or pharmaceutically acceptable salt thereof for use in the manufacture of a medicament for use in coadministration with another known inhibitor of HDAC, such as SAHA.

The compounds of the present invention can be used in both the treatment and prevention of cancer and can be used in a monotherapy or in a combination therapy. When used in a combination therapy, the compounds of the present invention are typically used together with small chemical compounds such as cisplatins, anti-metabolites, DNA topoisomerase inhibitors, radiation, antibody-based therapies (for example herceptin and rituximab), anti-cancer vaccination, gene therapy, cellular therapies, hormone therapies, radiation therapy or cytokine therapy.

In one embodiment of the invention, a compound of the invention is used in combination with another chemotherapeutic or antineoplastic agent in the treatment of a cancer. Examples of such other chemotherapeutic or antineoplastic agents include mitoxantrone, vinca alkaloids for example vincristine and vinblastine, anthracycline antibiotics for example daunorubicin and doxorubicin, alkylating agents for example chlorambucil and melphalan, taxanes for example paclitaxel, antifolates for example methotrexate and tomudex, epipodophyllotoxins for example etoposide, camptothecins for example irinotecan and its active metabolite SN 38 and DNA methylation inhibitors for example the DNA methylation inhibitors disclosed in WO02/085400.

According to the invention, therefore, products are provided which contain a compound of the invention and another chemotherapeutic or antineoplastic agent as a combined preparation for simultaneous, separate or sequential use in alleviating a cancer. Also provided according to the invention is the use of an FK228 analogue as defined above or an isostere thereof or a pharmaceutically acceptable salt thereof in the manufacture of a medicament for use in the alleviation of cancer by coadministration with another chemotherapeutic or antineoplastic agent. The compound of the invention and the said other agent may be administrated in any order. In both these cases, the compound of the invention and the other agent may be administered together or, if separately, in any order as determined by a physician.

HDAC is believed to contribute to the pathology and/or symptomology of several different diseases such that reduction of the activity of HDAC in a subject through inhibition of HDAC may be used to therapeutically address these disease states. Examples of various diseases that may be treated using the HDAC inhibitors of the present invention are described herein, and the use of compounds of the present invention described by Structure VII or VIII are included herein. It is noted that additional diseases beyond those disclosed herein may be later identified as applications of the compounds of the present invention, as the biological roles that HDAC play in various pathways becomes more fully understood.

One set of indications that HDAC inhibitors of the present invention may be used to treat are those involving undesirable or uncontrolled cell proliferation. Such indications include benign tumours, various types of cancers such as primary tumours and tumour metastasis, restenosis (e.g. coronary, carotid, and cerebral lesions), abnormal stimulation of endothelial cells (atherosclerosis), insults to body tissue due to surgery, abnormal wound healing, abnormal angiogenesis, diseases that produce fibrosis of tissue, repetitive motion disorders, disorders of tissues that are not highly vascularized, and proliferative responses associated with organ transplants. More specific indications for HDAC inhibitors include, but are not limited to prostate cancer, lung cancer, acute leukaemia, multiple myeloma, bladder carcinoma, renal carcinoma, breast carcinoma, colorectal carcinoma, neuroblastoma and melanoma.

In one embodiment, a method is provided for treating diseases associated with undesired and uncontrolled cell proliferation. The method comprises administering to a subject suffering from uncontrolled cell proliferation a therapeutically effective amount of a HDAC inhibitor according to the present invention, such that said uncontrolled cell proliferation is reduced. The particular dosage of the inhibitor to be used will depend on the severity of the disease state, the route of administration, and related factors that can be determined by the attending physician. Generally, acceptable and effective daily doses are amounts sufficient to effectively slow or eliminate uncontrolled cell proliferation.

HDAC inhibitors according to the present invention may also be used in conjunction with other agents to inhibit undesirable and uncontrolled cell proliferation. Examples of other anti-cell proliferation agents that may be used in conjunction with the HDAC inhibitors of the present invention include, but are not limited to, retinoid acid and derivatives thereof, 2-methoxyestradiol, ANGIOSTATIN™ protein, ENDOSTATIN™ protein, suramin, squalamine, tissue inhibitor of metalloproteinase-1, tissue inhibitor of metalloproteinase-2, plasminogen activator inhibitor-1, plasminogen activator inhibitor-2, cartilage-derived inhibitor, paclitaxel, platelet factor 4, protamine sulfate (clupeine), sulfated chitin derivatives (prepared from queen crab shells), sulfated polysaccharide peptidoglycan complex (sp-pg), staurosporine, modulators of matrix metabolism, including for example, proline analogs ((1-azetidine-2-carboxylic acid (LACA), cishydroxyproline, d,l-3,4-dehydroproline, thiaproline), beta.-aminopropionitrile fumarate, 4-propyl-5-(4-pyridinyl)-2(3H)-oxazolone; methotrexate, mitoxantrone, heparin, interferons, 2 macroglobulin-serum, chimp-3, chymostatin, beta.-cyclodextrin tetradecasulfate, eponemycin; fumagillin, gold sodium thiomalate, d-penicillamine (CDPT), beta-1-anticollagenase-serum, alpha.2-antiplasmin, bisantrene, lobenzarit disodium, n-(2-carboxyphenyl-4-chloroanthronilic acid disodium or "CCA", thalidomide; angostatic steroid, carboxyaminoimidazole; metalloproteinase inhibitors such as BB94. Other anti-angiogenesis agents that may be used include antibodies, preferably monoclonal antibodies against these angiogenic growth factors: βFGF, αFGF, FGF-5, VEGF isoforms, VEGF-C, HGF/SF and Ang-1/Ang-2. Ferrara N. and Alitalo, K. "Clinical application of angiogenic growth factors and their inhibitors" (1999) Nature Medicine 5:1359-1364.

Generally, cells in benign tumours retain their differentiated features and do not divide in a completely uncontrolled manner. A benign tumour is usually localized and nonmetastatic. Specific types of benign tumours that can be treated using HDAC inhibitors of the present invention include hemangiomas, hepatocellular adenoma, cavernous haemangioma, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas and pyogenic granulomas.

In the case of malignant tumors, cells become undifferentiated, do not respond to the body's growth control signals, and multiply in an uncontrolled manner. Malignant tumors are invasive and capable of spreading to distant sites (metastasizing). Malignant tumors are generally divided into two categories: primary and secondary. Primary tumors arise directly from the tissue in which they are found. Secondary tumors, or metastases, are tumors that originated elsewhere in the body but have now spread to distant organs. Common routes for metastasis are direct growth into adjacent structures, spread through the vascular or lymphatic systems, and tracking along tissue planes and body spaces (peritoneal fluid, cerebrospinal fluid, etc.).

Specific types of cancers or malignant tumors, either primary or secondary, that can be treated using the HDAC inhibitors of the present invention include, but are not limited to, leukaemia, breast cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuronms, intestinal ganglloneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythermia vera, adenocarcinoma, glioblastoma multiforma, leukemias, lymphomas, malignant melanomas, epidermoid carcinomas, and other carcinomas and sarcomas.

The HDAC inhibitors of the present invention may also be used to treat abnormal cell proliferation due to insults to body tissue during surgery. These insults may arise as a result of a variety of surgical procedures such as joint surgery, bowel surgery, and cheloid scarring. Diseases that produce fibrotic tissue include emphysema. Repetitive motion disorders that may be treated using the present invention include carpal tunnel syndrome. An example of a cell proliferative disorder that may be treated using the invention is a bone tumor.

Proliferative responses associated with organ transplantation that may be treated using HDAC inhibitors of the invention include proliferative responses contributing to potential organ rejections or associated complications. Specifically, these proliferative responses may occur during transplantation of the heart, lung, liver, kidney, and other body organs or organ systems.

Abnormal angiogenesis that may be may be treated using this invention include those abnormal angiogenesis accompanying rheumatoid arthritis, ischemic-reperfusion related brain edema and injury, cortical ischemia, ovarian hyperplasia and hypervascularity (polycystic ovary syndrome), endometriosis, psoriasis, diabetic retinopathy, and other ocular angiogenic diseases such as retinopathy of prematurity (retrolental fibroplastic), macular degeneration, corneal graft rejection, neuroscular glaucoma and Oster-Webber syndrome.

Examples of diseases associated with uncontrolled angiogenesis that may be treated according to the present invention include, but are not limited to retinal/choroidal neovascularization and corneal neovascularization. Examples of retinal/choroidal neovascularization include, but are not limited to, Best's diseases, myopia, optic pits, Stargart's diseases, Paget's disease, vein occlusion, artery occlusion, sickle cell anemia, sarcoid, syphilis, pseudoxanthoma elasticum carotid apo structive diseases, chronic uveitis/vitritis, mycobacterial infections, Lyme's disease, systemic lupus erythematosus, retinopathy of prematurity, Eales disease, diabetic retinopathy, macular degeneration, Bechets diseases, infections causing a retinitis or chroiditis, presumed ocular histoplasmosis, pars planitis, chronic retinal detachment, hyperviscosity syndromes, toxoplasmosis, trauma and post-laser complications, diseases associated with rubesis (neovascularization of the angle) and diseases caused by the abnormal proliferation of fibrovascular or fibrous tissue including all forms of proliferative vitreoretinopathy. Examples of corneal neovascularization include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, diabetic retinopathy, retinopathy of prematurity, corneal graft rejection, Mooren ulcer, Terrien's marginal degeneration, marginal keratolysis, polyarteritis, Wegener sarcoidosis, Scleritis, periphigoid radial keratotomy, neovascular glaucoma and retrolental fibroplasia, syphilis, Mycobacteria infections, lipid degeneration, chemical burns, bacterial ulcers, fungal ulcers, Herpes simplex infections, Herpes zoster infections, protozoan infections and Kaposi's sarcoma.

Chronic inflammatory diseases associated with uncontrolled angiogenesis may also be treated using HDAC inhibitors of the present invention. Chronic inflammation depends on continuous formation of capillary sprouts to maintain an influx of inflammatory cells. The influx and presence of the inflammatory cells produce granulomas and thus maintains the chronic inflammatory state. Inhibition of angiogenesis using a HDAC inhibitor alone or in conjunction with other anti-inflammatory agents may prevent the formation of the granulomas and thus alleviate the disease. Examples of chronic inflammatory diseases include, but are not limited to, inflammatory bowel diseases such as Crohn's disease and ulcerative colitis, psoriasis, sarcoidosis, and rheumatoid arthritis.

Inflammatory bowel diseases such as Crohn's disease and ulcerative colitis are characterized by chronic inflammation and angiogenesis at various sites in the gastrointestinal tract. For example, Crohn's disease occurs as a chronic transmural inflammatory disease that most commonly affects the distal ileum and colon but may also occur in any part of the gastrointestinal tract from the mouth to the anus and perianal area. Patients with Crohn's disease generally have chronic diarrhea associated with abdominal pain, fever, anorexia, weight loss and abdominal swelling. Ulcerative colitis is also a chronic, nonspecific, inflammatory and ulcerative disease arising in the colonic mucosa and is characterized by the presence of bloody diarrhea. These inflammatory bowel diseases are generally caused by chronic granulomatous inflammation throughout the gastrointestinal tract, involving new capillary sprouts surrounded by a cylinder of inflammatory cells. Inhibition of angiogenesis by these inhibitors should inhibit the formation of the sprouts and prevent the formation of granulomas. Inflammatory bowel diseases also exhibit extra intestinal manifestations, such as skin lesions. Such lesions are characterized by inflammation and angiogenesis and can occur at many sites other the gastrointestinal tract. Inhibition of angiogenesis by HDAC inhibitors according to the present invention can reduce the influx of inflammatory cells and prevent lesion formation.

Sarcoidosis, another chronic inflammatory disease, is characterized as a multisystem granulomatous disorder. The granulomas of this disease can form anywhere in the body. Thus, the symptoms depend on the site of the granulomas and whether the disease is active. The granulomas are created by the angiogenic capillary sprouts providing a constant supply of inflammatory cells. By using HDAC inhibitors according to the present invention to inhibit angionesis, such granulomas formation can be inhibited. Psoriasis, also a chronic and recurrent inflammatory disease, is characterized by papules and plaques of various sizes. Treatment using these inhibitors alone or in conjunction with other anti-inflammatory agents should prevent the formation of new blood vessels necessary to maintain the characteristic lesions and provide the patient relief from the symptoms.

Rheumatoid arthritis (RA) is also a chronic inflammatory disease characterized by non-specific inflammation of the peripheral joints. It is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis. Treatment using HDAC inhibitors according to the present invention alone or in conjunction with other anti-RA agents may prevent the formation of new blood vessels necessary to maintain the chronic inflammation.

The compounds of the present invention can further be used in the treatment of cardiac/vasculature diseases such as hypertrophy, hypertension, myocardial infarction, reperfusion, ischaemic heart disease, angina, arrythmias, hypercholestremia, atherosclerosis and stroke. The compounds can further be used to treat neurodegenerative disorders/CNS disorders such as acute and chronic neurological diseases, including stroke, Huntington's disease, Amyotrophic Lateral Sclerosis and Alzheimer's disease.

The compounds of the present invention can also be used as antimicrobial agents, for example antibacterial agents. The invention therefore also provides a compound for use in the treatment of a bacterial infection. The compounds of the present invention can be used as anti-infectious compounds against viral, bacterial, fungal and parasitic infections. Examples of infections include protozoal parasitic infections (including *plasmodium, cryptosporidium parvum, toxoplasma gondii, sarcocystis neurona* and *Eimeria* sp.)

The compounds of the present invention are particularly suitable for the treatment of undesirable or uncontrolled cell proliferation, preferably for the treatment of benign tumours/hyperplasias and malignant tumors, more preferably for the treatment of malignant tumors and most preferably for the treatment of CCL, breast cancer and T-cell lymphoma.

In a preferred embodiment of the invention, the compounds of the invention are used to alleviate cancer, cardiac hypertrophy, chronic heart failure, an inflammatory condition, a cardiovascular disease, a haemoglobinopathy, a thalassemia, a sickle cell disease, a CNS disorder, an autoimmune disease, diabetes, osteoporosis, MDS, benign prostatic hyperplasia, oral leukoplakia, a genetically related metabolic disorder, an infection, Rubens-Taybi, fragile X syndrome, or alpha-1 antitrypsin deficiency, or to accelerate wound healing, to protect hair follicles or as an immunosuppressant.

Typically, said inflammatory condition is a skin inflammatory condition (for example psoriasis, acne and eczema), asthma, chronic obstructive pulmonary disease (COPD), rheumatoid arthritis (RA), inflammatory bowel disease (IBD), Crohn's disease or colitis.

Typically, said cancer is chronic lymphocytic leukaemia, breast cancer, prostate cancer, ovarian cancer, mesothelioma or T-cell lymphoma.

Typically, said cardiovascular disease is hypertension, myocardial infarction (MI), ischemic heart disease (IHD) (reperfusion), angina pectoris, arrhythmia, hypercholestremia, hyperlipidaemia, atherosclerosis, stroke, myocarditis, congestive heart failure, primary and secondary i.e. dilated (congestive) cardiomyopathy, hypertrophic cardiomyopathy, restrictive cardiomyopathy, peripheral vascular disease, tachycardia, high blood pressure or thrombosis.

Typically, said genetically related metabolic disorder is cystic fibrosis (CF), peroxisome biogenesis disorder or adrenoleukodystrophy.

Typically, the compounds of the invention are used as an immunosuppressant following organ transplant.

Typically, said infection is a viral, bacterial, fungal or parasitic infection, in particular an infection by *S. aureus, P. acne, Candida* or *Aspergillus*.

Typically, said CNS disorder is Huntingdon's disease, Alzheimer's disease, multiple sclerosis or amyotrophic lateral sclerosis.

In this embodiment, the compounds of the invention may be used to alleviate cancer, cardiac hypertrophy, chronic heart failure, an inflammatory condition, a cardiovascular disease, a haemoglobinopathy, a thalassemia, a sickle cell disease, a CNS disorder, an autoimmune disease, diabetes or osteoporosis, or are used as an immunosuppressant.

The compounds of the invention may also be used to alleviate chronic lymphocytic leukaemia, breast cancer, prostate cancer, ovarian cancer, mesothelioma, T-cell lymphoma, cardiac hypertrophy, chronic heart failure or a skin inflammatory condition, in particular psoriasis, acne or eczema.

The compounds of the present invention can be used in the treatment of animals, preferably in the treatment of mammals and more preferably in the treatment of humans.

The compounds of the invention may, where appropriate, be used prophylactically to reduce the incidence of such conditions.

A therapeutically effective amount of a compound of the invention is administered to a patient. A typical dose is from about 0.001 to 50 mg per kg of body weight, according to the activity of the specific compound, the age, weight and condition of the subject to be treated, the type and severity of the disease and the frequency and route of administration.

The following Examples illustrate the invention. Compounds were prepared by general Schemes 3 and 4 shown below. Their structures were confirmed by various techniques, including NMR (details not given).

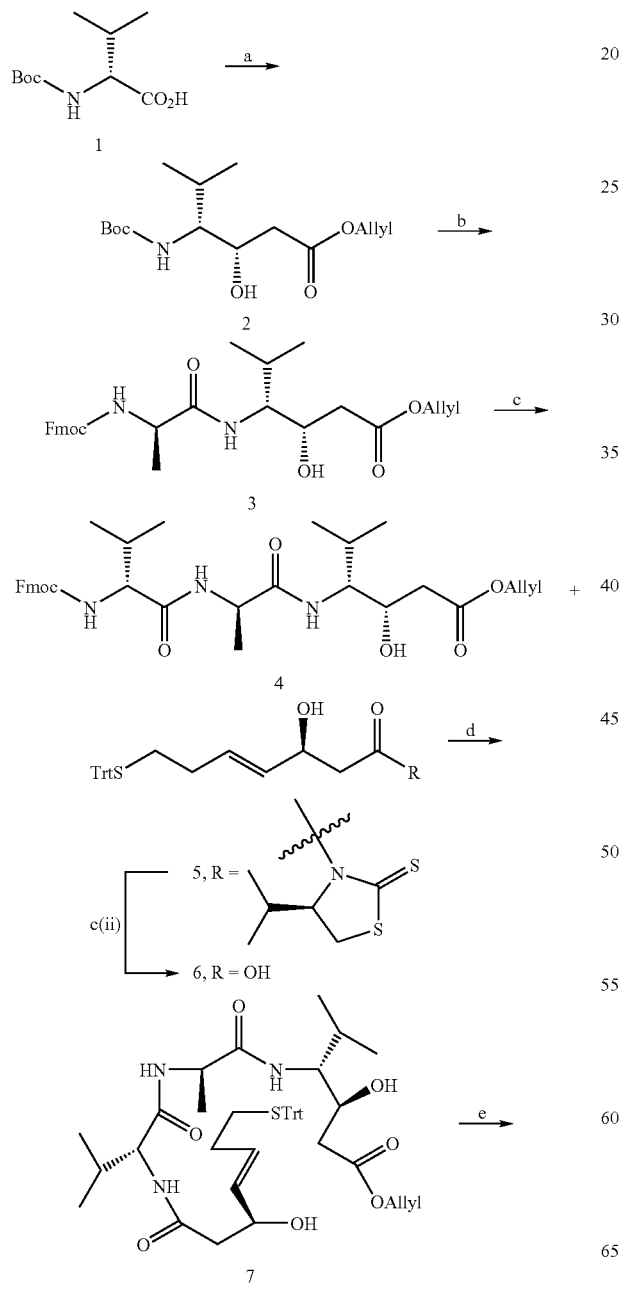

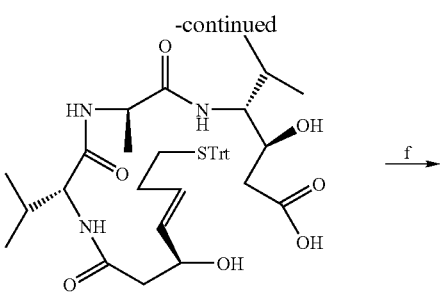

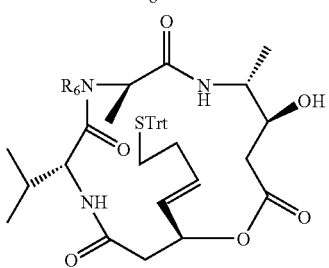

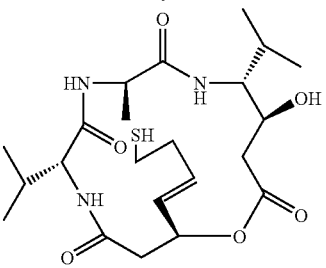

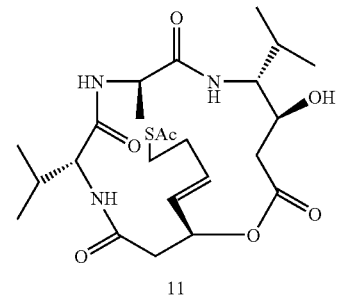

Preparation of (3S,4R)-4-[(R)-2-(3-9H-Fluoren-9-yl-propionylamino)-propionylamino]-3-hydroxy-5-methyl-hexanoic acid allyl ester (3)

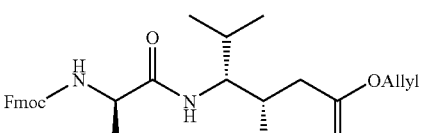

To a solution of 2 (316 mg, 1.05 mmol, prepared according to the procedure in Doi, T,; Iijima, Y.; Shin-ya, K.; Ganesan, A,; Takahashi, T.; *Tet. Lett.* 2006, 47, 1177-1080) in CH$_2$Cl$_2$ (5 mL) at 0° C. under argon was added TFA (2 mL, 40% v/v) and the reaction mixture was for 2 h 5 mins. After which time the solvent was removed in vacuo and put under high vacuum for 2 h. Then at 0° C. to a solution of PyBop (608 mg, 1.17 mmol) and Fmoc-D-Ala-OH (359.6 mg, 1.16 mmol) in CH$_2$Cl$_2$ (20 mL) was added diisopropylethylamine (0.71 mL, 4.1 mmol) under argon with stirring for 4 mins. This solution was then added to the deprotected amine of 2 in CH$_3$CN (20 mL) and the solution was stirred overnight for 16 h. The solvent was then removed in vacuo. Purification by column chromatography on silica (eluent 3:7-1:1 EtOAc/Hexane) gave 3 (330 mg, 0.67 mmol, 64%) as a white solid: R$_f$ 0.40 EtOAc/Hexane (6:4); IR (thin film) 3315 (b), 2962 (m), 1712 (s), 1660 (s), 1529 (s) cm$^{-1}$.

Preparation of (3S,4R)-4-{(R)-2-[(R)-2-(9H-Fluoren-9-ylmethoxycarbonylamino)-3-methyl-butyrylamino]-propionylamino}-3-hydroxy-5-methyl-hexanoic acid allyl ester (4)

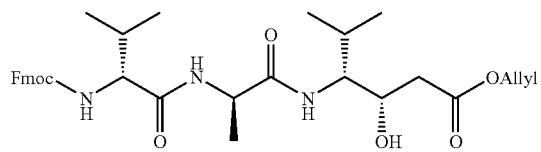

To a solution of 3 (162.1 mg, 0.33 mmol) in CH$_3$CN/CH$_2$Cl$_2$ (15:10 mL) was added diethylamine (2.5 mL, 10% v/v) under argon. After 1 h 15 mins the solvent was removed in vacuo and this was repeated with hexane (3×15 ml) after which time the crude material was put under a high vacuum for 4 h 45 mins. Then at 0° C. to Fmoc-D-Val-OH (124.6 mg, 0.37 mmol) and PyBop (191.1 mg, 0.37 mmol) in CH$_2$Cl$_2$ (20 mL) was added dropwise diisopropylethylamine (0.2 mL, 1.1 mmol). After 2 mins of stirring this solution was then added to the crude amine of 3 in CH$_3$CN (20 mL). The solvent was removed in vacuo and the solid formed was purified by column chromatography on silica (eluent 6:4-7:3-8:2 EtOAc/Hexane) to give 4 (165.5 mg, 0.28 mmol, 84%) as a white solid: R$_f$ 0.44 EtOAc/Hexane (6:4); IR (thin film) 3293 (b), 2963 (m), 1702 (m), 1642 (s), 1535 (m) cm$^{-1}$.

Preparation of (E)-(S)-3-Hydroxy-7-trisulfanylhept-4-enoic acid (6)

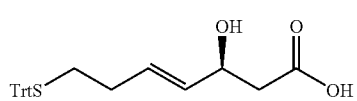

To a stirred solution of 5 (934 mg, 1.66 mmol, prepared according to the procedure in Yurek-George, A.; Habens, F.; Brimmell, M.; Packham, G.; Ganesan, A. *J. Am. Chem. Soc.* 2004, 126, 1030-1031) in THF/H$_2$O (39 mL, 3:1) was added lithium hydroxide (196.1 mg, 8.19 mmol) and allowed to stir for 50 mins. After which time 1M HCl was added until the pH reached 2, EtOAc (20 mL) was added and the layers were separated. The aqueous layer was extracted with EtOAc (20 mL) the organic layers were combined, dried (MgSO$_4$) and concentrated in vacuo. Purification by flash column chromatography (eluent 3:7-1:1-1:0 EtOAc/Hexane) gave the product 6 as a white solid (600 mg, 1.43 mmol, 86%): R$_f$ 0.52 EtOAc+2 drops AcOH; [α]$_D^{27}$ −4.15 (c 0.975, CH$_2$Cl$_2$.

Preparation of (3S,4R)-3-Hydroxy-4-{(R)-2-[(R)-2-((E)-(S)-3-hydroxy-7-tritylsulfanyl-hept-4-enoylamino)-3-methyl-butyrylamino]-propionylamino}-5-methyl-hexanoic acid allyl ester (7)

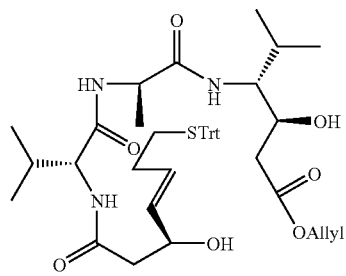

To a solution of 4 (165.5 mg, 0.28 mmol) in CH$_3$CN/CH$_2$Cl$_2$ (10:8 mL) was added diethylamine (1.8 mL, 10% v/v) under argon with stirring. After 1 h 30 mins the solvent was removed in vacuo and this was repeated with hexane (3×15 ml) after which time the crude material was put under a high vacuum for 1 h. Then at 0° C. to the β-hydroxy acid 6 (128.4 mg, 0.31 mmol) and PyBop (160 mg, 0.31 mmol) in CH$_2$Cl$_2$ (10 mL) was added dropwise diisopropylethylamine (0.13 mL, 0.75 mmol). After 5 min of stirring this solution was then added to the crude deprotected amine of 4 in CH$_3$CN (10 mL). Purification was then carried out by column chromatography on silica (eluent 8:2-9:1-1:0 EtOAc/Hexane) to give 7 (152.2 mg, 0.20 mmol, 70%) as a white solid: R$_f$ 0.12 EtOAc/Hexane (8:2); IR (thin film) 3269 (b), 2964 (w), 2930 (w), 1728 (m), 1622 (s), 1536 (m) cm$^{-1}$.

Preparation of (3S,4R)-3-Hydroxy-4-{(R)-2-[(R)-2-((E)-(S)-3-hydroxy-7-tritylsulfanyl-hept-4-enoylamino)-3-methyl-butyrylamino]-propionylamino}-5-methyl-hexanoic acid (8)

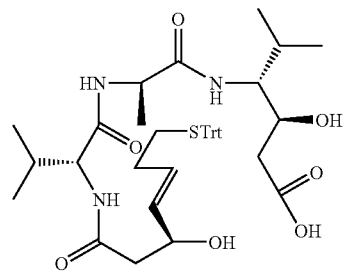

To a solution of 7 (152.2 mg, 0.2 mmol), Pd(PPh$_3$)$_4$ (23.2 mg, 0.02 mmol) in dry methanol (6 mL) under argon was added morpholine (35 μL, 0.40 mmol) which was allowed to stir for 2 h. The reaction mixture was concentrated in vacuo, purification by column chromatography on silica (eluent 0:1-5:95-10:90-10:90+0.5% AcOH MeOH/CH$_2$Cl$_2$) to give a yellow solid 8 (137 mg, 0.18 mmol, 100%): R$_f$ 0.19 MeOH/CH$_2$Cl$_2$ (1:9+0.5% AcOH); IR (thin film) 3271 (b), 2962 (m), 2926 (m), 1624 (s), 1536 (m) cm$^{-1}$.

Preparation of (3S,7R,10R,13R,14S)-14-Hydroxy-7, 13-diisopropyl-10-methyl-3-((E)-4-tritylsulfanyl-but-1-enyl)-1,2-dioxa-6,9,12-triaza-cyclohexadecane-5, 8,11,16-tetraone (9)

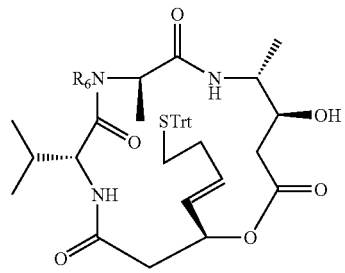

To a solution of MNBA (73.5 mg, 0.21 mmol) and DMAP (51.9 mg, 0.42 mmol) in CH$_2$Cl$_2$/THF (33 mL, 2:1) was added dropwise a solution of acid 8 (129 mg, 0.18 mmol) in CH$_2$Cl$_2$/THF (134.5 mL, 2:1) with 3 drops of DMF over 4 h. After a further 16 h the reaction mixture were concentrated in vacuo. Purification by flash column chromatography on silica (eluent 1:0-98:2-96:4-94:6-92.8 CH$_2$Cl$_2$/MeOH) gave 9 (24.7 mg, 0.035 mmol, 17%) as a white solid: R$_f$ 0.43 CH$_2$Cl$_2$/MeOH (90:10); IR (thin film) 3293 (b), 2963 (m), 1732 (m), 1660 (s), 1536 (m) cm$^{-1}$.

Preparation of (3S,7R,10R,13R,14S)-14-Hydroxy-7, 13-diisopropyl-3-((E)-4-mercapto-but-1-enyl)-10-methyl-1,2-dioxa-6,9,12-triaza-cyclohexadecane-5,8, 11,16-tetraone (10)

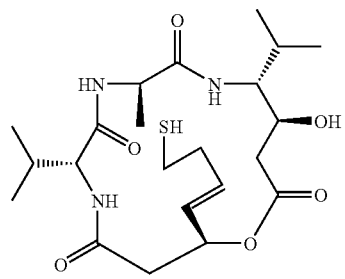 [SMILES: CC(C)[C@H]1NC(=O)[C@@H](C)NC(=O)[C@@H](C(C)C)NC(=O)C[C@@H](/C=C/CCS)OC(=O)C[C@@H]1O]

To a solution of 9 (8 mg, 0.011 mmol) in CH$_2$Cl$_2$ (1 mL) was added triethylsilane (7 µL, 0.44 mmol) was added dropwise TFA (0.2 mL, 20% v/v). After stirring for 1.5 h the reaction was concentrated in vacuo and purified by flash column chromatography (eluent 1:0-99:1-98:2-97:3-96.4 CH$_2$Cl$_2$/MeOH) to give the product 10 (0.47 mg, 0.001 mmol, 9%) as a white solid: R$_f$ 0.44 MeOH/CH$_2$Cl$_2$ (1:9); MS (ES$^+$) 584.2 (100%, [M+Na]$^+$).

Preparation of Thioacetic acid S-[(E)-4-((3S,7R,10R, 13R,14S)-14-hydroxy-7,13-diisopropyl-10-methyl-5, 8,11,16-tetraoxo-1,2-dioxa-6,9,12-triaza-cyclohexadec-3-yl)-but-3-enyl]ester (11)

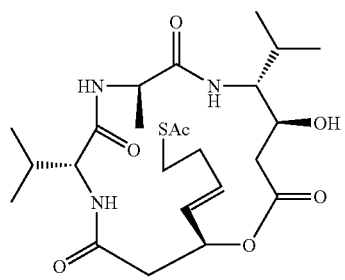

To a solution of 9 (24.7 mg, 0.035 mmol) in CH$_2$Cl$_2$ (1.4 mL) was added triethylsilane (28 µL, 0.175 mmol) followed by the dropwise addition of TFA (0.35 mL, 25% v/v). After stirring for 1 h the reaction mixture was concentrated in vacuo and put under high vacuum for 2 h to give the crude thiol 10. At 0° C. to a solution of thiol 10 in CH$_2$Cl$_2$ (0.45 mL) was added diisopropylethylamine (30 µL, 0.172 mmol) followed by acetyl chloride (2.43 µL, 0.034 mmol) in CH$_2$Cl$_2$ (0.1 mL). After stirring for 2 h 10 min 1M HCl (1 mL) was added followed by EtOAc (10 mL) the layers were separated and the organic layer was washed with sat. brine (10 mL). The organic layer was dried (MgSO$_4$) and concentrated in vacuo. Purification by flash column chromatography (eluent 1:0-98: 2-96:4-94:6-92.8 CH$_2$Cl$_2$/MeOH) gave the product 11 (7.3 mg, 0.014 mmol, 41%) as a white solid: R$_f$ 0.47 MeOH/CH$_2$Cl$_2$ (1:9).

Scheme 4

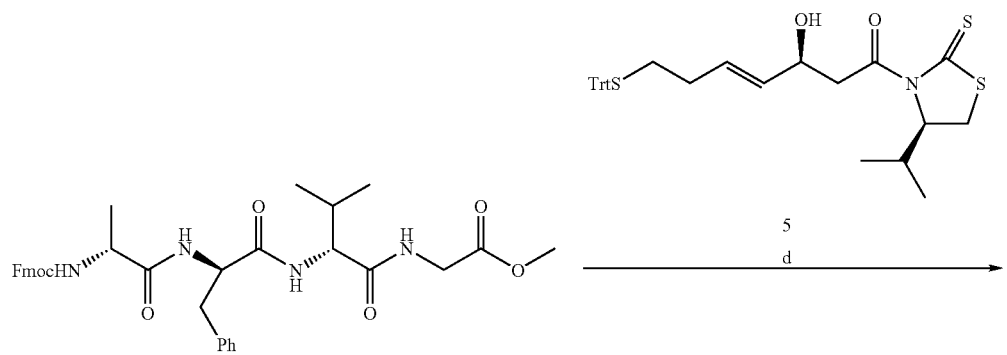

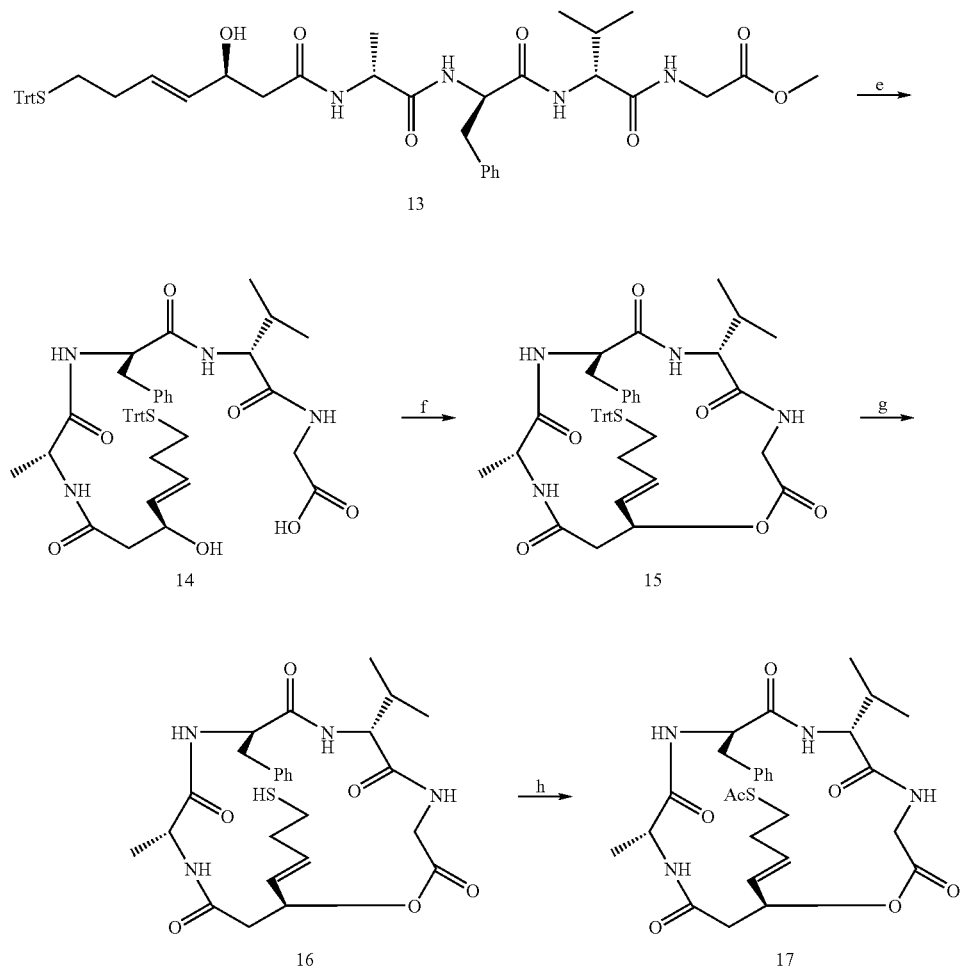

Preparation of ((R)-2-{(R)-2-[(R)-2-((E)-(R)-3-Hydroxy-7-tritylsulfanyl-hept-4-enoylamino)-propionylamino]-3-phenyl-propionylamino}-3-methyl-butyrylamino)-acetic acid methyl ester (13)

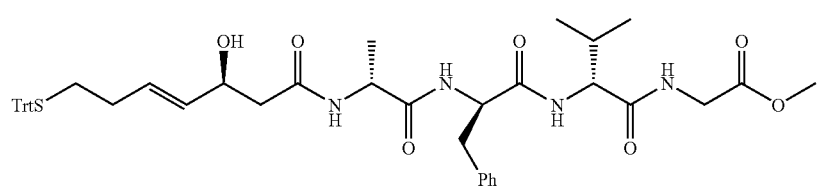

To a solution of the tetrapeptide 12 (159 mg, 0.391 mmol, purchased from GLBiochem Ltd, Shanghai 200241, China) in CH$_3$CN (7 mL) was added a solution of 5 (242 mg, 0.43 mmol) dissolved in CH$_2$Cl$_2$ (3 mL) followed by DMAP (4.78 mg, 0.0391 mmol). The reaction mixture was stirred overnight; the crude material was then concentrated in vacuo and the residue was purified by flash column chromatography on silica gel (eluent 1% MeOH/CH$_2$Cl$_2$) to give 13 (190 mg, 0.236 mmol, 60%) as a white solid: R$_f$ 0.28 MeOH/CH$_2$Cl$_2$ (5:95).

Preparation of ((R)-2-{(R)-2-[(R)-2-((E)-(R)-3-Hydroxy-7-tritylsulfanyl-hept-4-enoylamino)-propionylamino]-3-phenyl-propionylamino}-3-methyl-butyrylamino)-acetic acid (14)

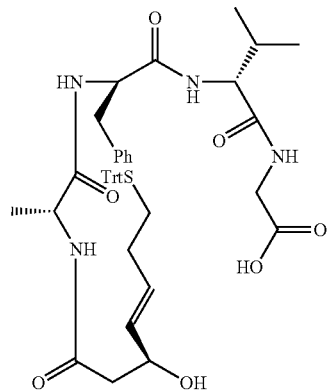

To a solution of 13 (190 mg, 0.236 mmol) in THF (4 mL) was added a solution of LiOH (8.48 mg, 0.354 mmol) in H$_2$O (1 mL) at 0° C. After stirring for 1 h CHCl$_3$ (60 mL) was added to the solution followed by 1M HCl (10 mL). The layers were separated and the aqueous phase washed with CHCl$_3$ (2×10 mL). The organic layers were combined, washed with brine, dried with MgSO$_4$ and concentrated in vacuo. The crude material was then purified by flash column chromatography on silica gel (eluent 2% MeOH/CH$_2$Cl$_2$) to give 14 (80 mg, 0.1 mmol, 43%) as a pale yellow solid: R$_f$ 0.21 AcOH/MeOH/CH$_2$Cl$_2$/(1:4:95).

Preparation of (6R,9R,12R,16S)-9-Benzyl-6-isopropyl-12-methyl-16-((E)-4-tritylsulfanyl-but-1-enyl)-1-oxa-4,7,10,13-tetraaza-cyclohexadecane-2,5,8,11,14-pentaone (15)

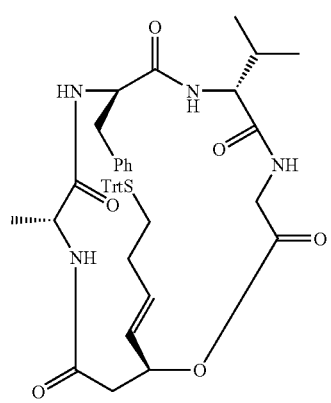

To a solution of 2-methyl-6-nitrobenzoic anhydride (MNBA) (43.7 mg, 0.127 mmol) and DMAP (29.9 mg, 0.245 mmol) in CH$_2$Cl$_2$ (26 mL) was added dropwise a solution of acid 14 (80 mg, 0.10 mmol) dissolved in CH$_2$Cl$_2$ (88 mL) and DMF (5 mL) over 3 hours and the reaction was stirred overnight. Finally the reaction mixture was concentrated in vacuo and the residue was purified by flash column chromatography on silica gel (eluent 1-3% MeOH/CH$_2$Cl$_2$) to give 15 (26.5 mg, 0.034 mmol, 34%) as a white solid: R$_f$ 0.35 MeOH/CH$_2$Cl$_2$ (5:95).

Preparation of (6R,9R,12R,16S)-9-Benzyl-6-isopropyl-16-((E)-4-mercapto-but-1-enyl)-12-methyl-1-oxa-4,7,10,13-tetraaza-cyclohexadecane-2,5,8,11,14-pentaone (16)

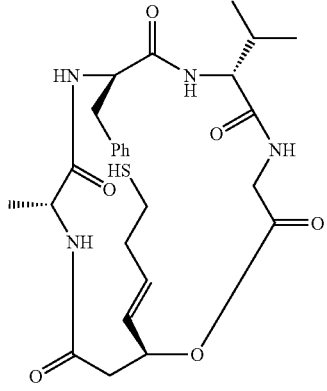 [SMILES: CC(C)[C@H]1NC(=O)[C@@H](Cc2ccccc2)NC(=O)[C@@H](C)NC(=O)C[C@@H](/C=C/CCS)OC(=O)CNC1=O]

To a stirred solution of 15 (9 mg, 0.012 mmol) in CH$_2$Cl$_2$ (500 µL) Et$_3$SiH (3.83 µL, 0.024 mmol) and TFA (60 µL) were added. After 15 minutes stirring the solvent was removed in vacuo and the residue was purified by flash column chromatography on silica gel (2-7% MeOH/CH$_2$Cl$_2$) to give thiol 16 (2.3 mg, 0.0043 mmol, 36%) as a white solid: R$_f$ 0.58 MeOH/CH$_2$Cl$_2$ (1:9); LRMS (ES$^+$) m/z 555.4 (100%, [M+Na]$^+$).

Preparation of Thioacetic acid S-[(E)-4-((6R,9R,12R,16S)-9-benzyl-6-isopropyl-12-methyl-2,5,8,11,14-pentaoxo-1-oxa-4,7,10,13-tetraaza-cyclohexadec-16-yl)-but-3-enyl]ester (17)

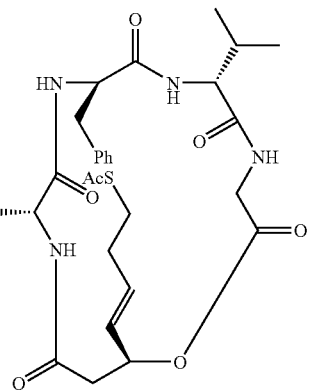

To a stirred solution of 15 (15 mg, 19 µmol) in CH$_2$Cl$_2$ (0.8 mL) was added Et$_3$SiH (16 µL, 0.1 mmol) and TFA (0.2 mL). After stirring at room temperature for 30 minutes under an inert atmosphere, the reaction mixture was concentrated and the residue dried by high vacuum. Without further purification, the crude thiol 16 was used in next step. At 0° C., to a stirred solution of thiol 16 in CH$_2$Cl$_2$ (0.3 mL) was added DIPEA (17 µL, 0.1 mmol) and AcCl (2 µL, 28 µmol). After 30 minutes the reaction mixture was warmed to rt and stirred for a further 1.5 h, whereupon it was quenched by addition of 1M HCl (1 mL). EtOAc (5 mL) was added to dilute the solution, phases separated, and the aqueous phase extracted with EtOAc (2×1 mL). The combined organic phases were washed with sat. aq NaCl (2 mL), dried (MgSO$_4$), filtered, and concentrated in vacuo. The residue was purified by flash chromatography (eluent: 1-10% IPA/CH$_2$Cl$_2$) to give compound 17 (5 mg, 8 μmol, 45%) as an off white solid.

Assay

In vitro HDAC assays were performed using a HDAC fluorescent activity assay kit (Biomol, UK) according to the manufacturer's instructions. Compounds were reduced prior to analysis; 1 mM compound was reduced with 30 mM DTT in DMSO overnight at room temperature, protected from light. Reactions were then set up in a 96-well plate. For each reaction 10 μl compound (5× required concentration in assay buffer) was mixed with 15 ml diluted Hela Nuclear Extract (30-fold in assay buffer). Serial dilutions were set up for each compound. Reactions containing Hela extract only and assay buffer only were also set up. 25 μl diluted Fluor de Lys™ substrate (100-fold in assay buffer) was added to each reaction, which were then incubated at 37° C. for 1 hour. The reaction was stopped by addition of 50 μl Fluor de Lys™ Developer (20-fold dilution in assay buffer, plus TSA diluted 100-fold). The reactions were then incubated at room temperature for 10 minutes before fluorescence was measured using a CytoFluor II Fluorescence Multiwell Plate Reader and CytoFluor II software with filters set at 360 nM for excitation and 460 nM for emission. Inhibition of in vitro HDAC activity was determined for mean values of duplicate samples as percentages relative to HeLa extract only reactions. IC$_{50}$ values were calculated using GraphPad Prism software. The results are shown in the following Table.

| Compound No. | IC$_{50}$ (nM) |
|---|---|
| 10 | 4.4 ± 0.45 |
| 11 | 21.63 ± 6.0 |
| 16 | 47 ± 9.9 |
| 17 | 126 ± 5.3 |

The invention claimed is:

1. A compound of the general Structure VII

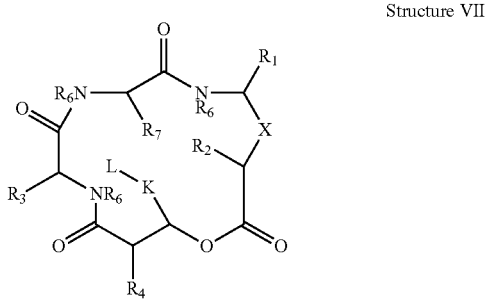

Structure VII

Including pharmaceutically acceptable salts thereof, wherein

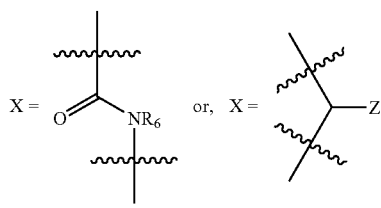

R$_1$, R$_2$ (where X=—CONR$_6$—), and R$_3$ are the same or different and each represents an amino-acid side chain moiety selected from the group consisting of: —H, —C$_1$-C$_6$ alkyl, —C$_2$-C$_6$ alkenyl, -L'-O—C(O)—R', -L"-C(O)—O—R", -L'-A, -L'-NR"R", -L-Het-C(O)-Het-R" and -L'-Het-R", wherein L' is a C$_2$-C$_6$ alkylene group and A is phenyl or a 5- to 6-membered heteroaryl group, each R' is the same or different and represents C$_1$-C$_4$ alkyl, each R" is the same or different and represents H or C$_1$-C$_6$ alkyl, each Het is the same or different and is a heteroatom spacer selected from —O—, —N(R''')— and —S—, and each R''' is the same or different and represents H or C$_1$-C$_4$ alkyl;

R$_7$ is selected from —H, —C$_1$-C$_6$ alkyl, —C$_2$-C$_6$ alkenyl or -L'-A;

R$_2$ (where X=—CHZ—), R$_4$ and R$_6$ are the same or different and each represents hydrogen, C$_1$-C$_6$ alkyl, C$_2$-C$_6$ alkenyl or, C$_2$-C$_6$ alkynyl;

K represents a linear or branched chain of 1-10 atoms containing carbon atoms and other atoms;

L represents SPr$^1$, wherein Pr$^1$ is H or a protecting group that forms a thioether, a monothio, dithio or aminothioacetal, a thioester or a carbamine acid thioester to protect a thiol group; and Z is a heteroatom bonded to the macrocycle by a single or double bond, and any other group bonded to Z is H or a protecting group.

2. The compound according to claim 1, wherein X is —CO—NR$_6$—.

3. The compound according to claim 1, wherein X is —CHZ—.

4. The compound according to claim 1, wherein Z is =O, —OPr$^3$, —N(Pr$^3$)Pr$^4$ or —SPr$^3$, and Pr$^3$ and Pr$^4$ are the same or different and each represents H or a heteroatom-protecting group such that Z is an ether, an ester, an amide, a thioether or a thioester.

5. The compound according to claim 1, wherein R$_1$ is —(C$_1$-C$_4$ alkyl)-A', or R$_3$ is —C$_2$-C$_4$ alkyl or —(C$_1$-C$_4$ alkyl)-A", wherein A' or A" is a C$_6$-C$_{10}$ aryl group or a 5- to 10-membered heteroaryl group.

6. The compound according to claim 5, wherein A' is phenyl and A" is phenyl, indolyl or t-butoxycarbonylindolyl.

7. The compound according to claim 6, wherein A is phenyl.

8. The compound according to claim 1, wherein -Het- is —O— or —NR'''.

9. The compound according to claim 1, wherein R$_1$ is selected from —H and —C$_1$-C$_6$ alkyl.

10. The compound according to claim 1, wherein R$_2$ is selected from —H and —C$_1$-C$_4$ alkyl.

11. The compound according to claim 1, wherein R$_3$ is selected from —H, —C$_1$-C$_6$ alkyl, -L'-C(O)—O—R", -L'-A, -L'-NR"R" and -L'-N(R")—C(O)—O—R".

12. The compound according to claim 1, wherein R$_4$ is selected from —H and —C$_1$-C$_4$ alkyl.

13. The compound according to claim 1, wherein R$_6$ is —H.

14. The compound according to claim 1, wherein Pr$^1$ is —H or a protecting group selected from a benzyl group which is optionally substituted by C$_1$-C$_6$ alkoxy, C$_1$-C$_6$ acyloxy, hydroxyl, nitro, picolyl, picolyl-N-oxide, anthrylmethyl, diphenylmethyl, phenyl, t-butyl, adamanthyl, C$_1$-C$_6$ acyloxymethyl, C$_1$-C$_6$ alkoxymethyl, tetrahydropyranyl, benzylthiomethyl, phenylthiomethyl, thiazolidinyl, acetamidomethyl, benzamidomethyl, t-butoxycarbonyl, acetyl, benzoyl, carbamoyl, phenylcarbamoyl and C$_1$-C$_6$ alkylcarbamoyl.

15. The compound according to claim 14, wherein Pr$^1$ is —H.

16. The compound according to claim 1, wherein each amino acid side chain is as present in a natural amino acid or is —(CH$_2$)$_2$—C(O)—O—C(CH$_3$)$_3$, —(CH$_2$)$_4$—NH—C(O)—O—C(CH$_3$)$_3$, —(CH$_2$)$_3$—NH—C(O)NH$_2$, —CH$_2$—CH$_2$OH or —(CH$_2$)$_2$—CH$_2$NH$_2$.

17. The compound according to claim 1, of formula 9, 10, 11, 15, 16 or 17:

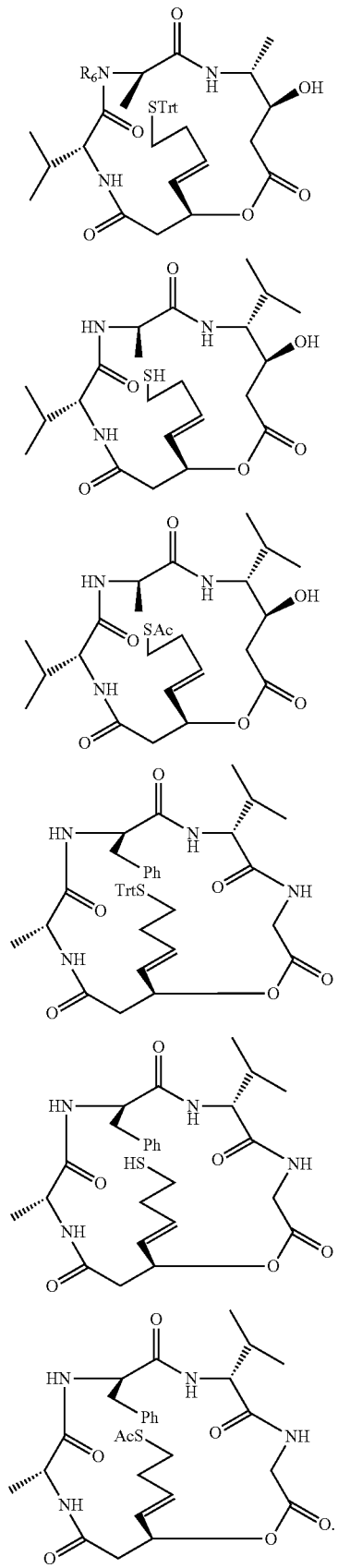

18. A method for treating wounds, wherein said method comprising administering to a subject in need thereof a compound of claim 1.

19. A pharmaceutical composition comprising a compound according to claim 1, and a pharmaceutically acceptable carrier or diluent.

20. The composition according to claim 19, which is in a form suitable for oral, rectal, parenteral, intranasal or transdermal administration or administration by inhalation or by suppository.

21. The composition according to claim 20, which is in the form of granules, a tablet, a capsule, a troche, a lozenge, an aqueous or oily suspension, or a dispersible powder.

22. The composition according to claim 19, further comprising another inhibitor of HDAC.

23. The composition, according to claim 19, further comprising another chemotherapeutic or antineoplastic agent.

24. A compound of the general Structure VIII

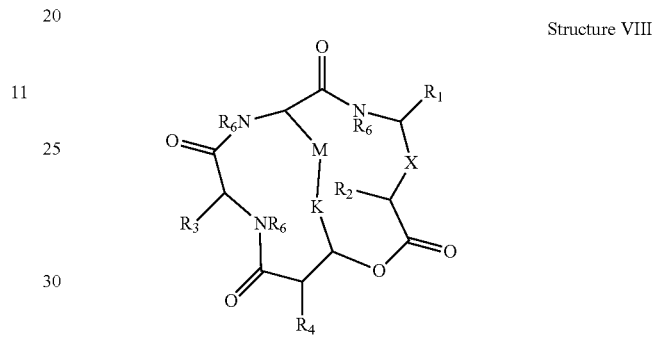

Structure VIII including pharmaceutically acceptable salts thereof, wherein

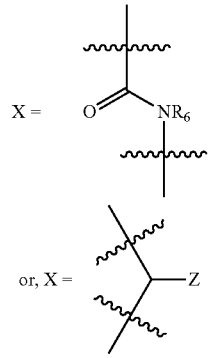

$R_1$, $R_2$ (where X=—$CONR_{6-}$), and $R_3$ are the same or different and each represents an amino-acid side chain moiety selected from the group consisting of: —H, —$C_1$-$C_6$ alkyl, —$C_2$-$C_6$ alkenyl, -L'-O—C(O)—R', -L'-C(O)—O—R", -L'-A, -L'-N R"R", -L'-Het-C(O)-Het-R" and -L'-Het-R", wherein L' is a $C_2$-$C_6$ alkylene group and A is phenyl or a 5- to 6-membered heteroaryl group, each R' is the same or different and represents $C_1$-$C_4$ alkyl, each R" is the same or different and represents H or $C_1$-$C_6$ alkyl, each Het is the same or different and is a heteroatom spacer selected from —O—, —N(R")— and —S—, and each R'" is the same or different and represents H or $C_1$-$C_4$ alkyl;

Z is a heteroatom bonded to the macrocycle by a single or double bond, and any other group bonded to Z is H or a protecting group;

$R_2$ (where X=—CHZ—), $R_4$ and $R_6$ are the same or different and each represents hydrogen, $C_1$-$C_6$ alkyl, $C_2$-$C_6$ alkenyl or, $C_2$-$C_6$ alkynyl;

K represents a linear or branched chain of 1-10 atoms containing carbon atoms and other atoms;

M is a linear or branched chain containing 1-10 carbon or other atoms, and is capable of undergoing in vivo cleavage to give the following Structure VII:

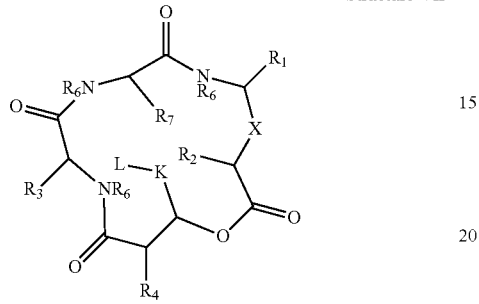

Structure VII wherein the variables are as defined above and $R_7$ is selected from —H, —$C_1$-$C_6$ alkyl, —$C_2$-$C_6$ alkenyl or -L'-A and L represents $SPr^1$, wherein $Pr^1$ is H or a protecting group that forms a thioether, a monothio, dithio or aminothioacetal, a thioester or a carbamine acid thioester to protect a thiol group.

* * * * *

UNITED STATES PATENT AND TRADEMARK OFFICE
CERTIFICATE OF CORRECTION

PATENT NO. : 8,865,655 B2
APPLICATION NO. : 12/516110
DATED : October 21, 2014
INVENTOR(S) : Arasu Ganesan et al.

It is certified that error appears in the above-identified patent and that said Letters Patent is hereby corrected as shown below:

In The Claims

Column 31,
Line 67, "-L'-O-C(O)-R',-L"- " should read -- -L'-O-C(O)-R', -L' --.

Signed and Sealed this
Tenth Day of February, 2015

Michelle K. Lee
*Deputy Director of the United States Patent and Trademark Office*